(12) United States Patent
Chudy et al.

(10) Patent No.: US 9,129,245 B2
(45) Date of Patent: *Sep. 8, 2015

(54) ADAPTIVE PHARMACEUTICAL PRODUCT MANAGEMENT METHODS AND SYSTEM

(75) Inventors: Duane S. Chudy, Lincolnshire, IL (US); James J. Wiczer, Buffalo Grove, IL (US)

(73) Assignee: Chudy Group, LLC, Chicago, IL (US)

( * ) Notice: Subject to any disclaimer, the term of this patent is extended or adjusted under 35 U.S.C. 154(b) by 606 days.

This patent is subject to a terminal disclaimer.

(21) Appl. No.: 13/442,254

(22) Filed: Apr. 9, 2012

(65) Prior Publication Data
US 2012/0239422 A1 Sep. 20, 2012

Related U.S. Application Data

(63) Continuation of application No. 12/185,510, filed on Aug. 4, 2008, now Pat. No. 8,165,929.

(51) Int. Cl.
| | |
|---|---|
| *G06Q 10/08* | (2012.01) |
| *G06F 19/00* | (2011.01) |
| *G07F 11/62* | (2006.01) |
| *G07F 17/00* | (2006.01) |

(52) U.S. Cl.
CPC ............ *G06Q 10/08* (2013.01); *G06F 19/3462* (2013.01); *G06Q 10/087* (2013.01); *G07F 11/62* (2013.01); *G07F 17/0092* (2013.01)

(58) Field of Classification Search
CPC .. G06Q 10/08; G06Q 10/087; G06F 19/3462; G07F 11/62; G07F 17/0042
See application file for complete search history.

(56) References Cited

U.S. PATENT DOCUMENTS

| | | | |
|---|---|---|---|
| 4,847,764 | A | 7/1989 | Halvorson |
| 4,936,738 | A | 6/1990 | Brennan et al. |
| 5,597,995 | A | 1/1997 | Williams et al. |
| 5,666,492 | A | 9/1997 | Rhodes et al. |
| 5,713,485 | A | 2/1998 | Liff et al. |

(Continued)

OTHER PUBLICATIONS

U.S. Appl. No. 13/004,730, filed Jan. 11, 2011, Chudy.

(Continued)

*Primary Examiner* — Asfand Sheikh
(74) *Attorney, Agent, or Firm* — Jansson Munger McKinley and Shape Ltd.

(57) ABSTRACT

Methods and systems for adaptive storage and management of pharmaceutical product containers at a pharmacy are described. Pharmaceutical product containers are managed so that the containers for more-frequently-used pharmaceutical products are stored among plural storage locations more-efficiently accessible to a pharmacy workstation. Containers for less-frequently-used pharmaceutical products are managed so that the containers for such products are stored among the storage locations which are less-accessible to the pharmacy workstation. As the frequency of pharmaceutical product usage changes, the inventory of pharmaceutical product containers is managed adaptively so that the containers used most frequently are stored at locations more-easily accessible to the pharmacy workstation, thereby facilitating fulfillment of prescriptions by pharmacy personnel. Further efficiencies may be achieved through use of an optical positioning system providing directed placing and picking of pharmaceutical product containers. Management of pharmaceutical product containers repeatedly taken from and returned to inventory may be provided.

26 Claims, 14 Drawing Sheets

(56) References Cited

U.S. PATENT DOCUMENTS

| | | | |
|---|---|---|---|
| 5,713,487 | A | 2/1998 | Coughlin |
| 5,737,539 | A | 4/1998 | Edelson et al. |
| 5,758,095 | A | 5/1998 | Albaum et al. |
| 5,762,235 | A | 6/1998 | Coughlin |
| 5,797,515 | A | 8/1998 | Liff et al. |
| 5,883,370 | A | 3/1999 | Walker et al. |
| 5,907,493 | A | 5/1999 | Boyer et al. |
| 5,993,046 | A | 11/1999 | McGrady et al. |
| 6,021,392 | A | 2/2000 | Lester et al. |
| 6,068,156 | A | 5/2000 | Liff et al. |
| 6,112,182 | A | 8/2000 | Akers et al. |
| 6,152,364 | A | 11/2000 | Schoonen et al. |
| 6,155,485 | A | 12/2000 | Coughlin et al. |
| 6,170,230 | B1 | 1/2001 | Chudy et al. |
| 6,181,979 | B1 | 1/2001 | Murakami |
| 6,202,923 | B1 | 3/2001 | Boyer et al. |
| 6,219,587 | B1 | 4/2001 | Ahlin et al. |
| 6,256,967 | B1 | 7/2001 | Hebron et al. |
| 6,318,630 | B1 | 11/2001 | Coughlin et al. |
| 6,330,491 | B1 | 12/2001 | Lion |
| 6,352,200 | B1 | 3/2002 | Schoonen et al. |
| 6,370,841 | B1 | 4/2002 | Chudy et al. |
| 6,438,451 | B1 | 8/2002 | Lion |
| RE37,829 | E | 9/2002 | Charhut et al. |
| 6,449,927 | B2 | 9/2002 | Hebron et al. |
| 6,529,801 | B1 | 3/2003 | Rosenblum |
| 6,625,952 | B1 | 9/2003 | Chudy et al. |
| 6,650,225 | B2 | 11/2003 | Bastian, II et al. |
| 6,762,382 | B1 | 7/2004 | Danelski |
| 6,762,681 | B1 | 7/2004 | Danelski |
| 6,847,861 | B2 | 1/2005 | Lunak et al. |
| 6,942,146 | B2 | 9/2005 | Pfutzenreuter et al. |
| 7,195,156 | B2 | 3/2007 | Venema et al. |
| 7,349,858 | B1 | 3/2008 | McGrady et al. |
| 8,165,929 | B2 | 4/2012 | Chudy et al. |
| 8,306,651 | B2 | 11/2012 | Chudy et al. |
| 2001/0002448 | A1 | 5/2001 | Wilson et al. |
| 2003/0149599 | A1 | 8/2003 | Goodall et al. |
| 2003/0225595 | A1 | 12/2003 | Helmus et al. |
| 2004/0088187 | A1 | 5/2004 | Chudy et al. |
| 2005/0125097 | A1 | 6/2005 | Chudy et al. |
| 2005/0149226 | A1 | 7/2005 | Stevens et al. |
| 2007/0065259 | A1 | 3/2007 | Talley |
| 2007/0173971 | A1 | 7/2007 | Richards et al. |
| 2010/0014950 | A1 | 1/2010 | Blackmore |

OTHER PUBLICATIONS

Vidyut H. Vashi, et al., "The Use of Response Surface Methodology to Optimize Logistics Simulation Models", Journal of Business Logistics. Date: 1995, Relevant page: p. 1, paragraphs 1-3.

Norman Saenz, Jr., "Perspectives on Material Handling Practice Developing Your Large Load Storage Area", Material Handling Institute, Charlotte, NC. Date: 2001, Relevant pages: Introduction and pp. 1-3.

Norman Saenz, Jr., "Four Walls, No Windows", Multichannel Merchant Internet article, <multichannelmerchant.com/opsandfulfillment/warehouse/fulfillment_four_wall_no/>, Date: 2001. Relevant pages: pp. 3-4.

"Warehouse Master Windows," Internet product description, <www.howardway.com/sw_wm2.html>, Howard Way and Associates, Baltimore, MD. Date: Copyright 1999, Relevant pages: pp. 2-3.

"PillPick Manager Automated Drug Management System Software," Internet product description, <www.swisslog.com>, Swisslog. Date: Copyright 2005, Relevant page: p. 1, paragraph 4.

"Powerhouse/WMS," Internet product description, <www.qssi-wms.com/phFuncOP.asp>, Quality Software Systems Inc. Date: Copyright 1985-2008. Relevant pages: pp. 1-3.

"Stock Track plus Warehouse Management System" brochure, ATMS plc, Birmingham, UK. Date: 2005. Relevant pages: pp. 3, 7, 9-10, 12, 14, 18-19, and 21.

ShelfLogic planogram Internet software product description, <www.shelflogic.com/product_comparison.htm>, Shelf Logic Software Products, Rock Hill, NY. Date: 2008, Relevant page: p. 1.

"Extended Warehouse Mangement with SAP Supply Chain Management" brochure, SAP A.G. Date: Copyright 2007. Relevant pages: pp. 4 and 8.

Serdar Z. Elgun, "Storage Operations" Internet article, <http://info.lu.farmingdale.edu/depts/met/ind315/storageoperations.html>. Date: 1999. Relevant pp. 1-7.

"Frequently Asked Questions: Rx Optimzier" Internet excerpts, <www.pharmhs.com/company/print_faqs.cfm?topic=26>, Pharmacy Healthcare Solutions. Date: 2004, Relevant pages: pp. 1 and 2.

"Distribution Management Slotting Optimization" brochure, Manhattan Associates, Atlanta, GA. Date: 2008. Relevant pages: pp. 1 and 2.

"Microsoft Dynamics AX" brochure, Microsoft Corporation, Redmond, WA. Date: Copyright 2004. Relevant pages: p. 3.

"Pick to Light (PTL)" Internet product description, <www.bastiansolutions.com/products/pick-to-light/default.asp>, BMH, LLC. Date: Copyright 2008, Relevant pages: pp. 1, 4-6.

"Automated Storage and Retrieval Systems" Internet product description, <www.bastiansolutions.com/products/automated-storage-and-retrieval-systems/default.asp>, BMH, LLC. Date: Copyright 2008. Relevant pp. 1, 4-5 and 8-9.

"Pick Max 2" Internet product description, <www.ipti.net>, Innovative Picking Technologies, Inc., Ixonia, WI. Date: 2008. Relevant page: p. 1.

"Econo-Pick Light Directed Order Fulfillment System" Internet product description, <www.vistamation.com>, Innovative Picking Technologies, Inc., Ixonia, WI. Date: 2008.

"Controls and Automation Interfaces" brochure, ASAP Automation, LLC, Louisville, KY. Date: 2008. Relevant pages: pp. 53, 56-63 and 68.

"See the Light" Internet product description, <www.lighthouseselection.com>, Lighthouse Selection, LLC. Date: Copyright 2006.

"Pick to Light" Internet product description, <http//www.weinet.com/Pick-to-Light.asp>, Warehouse Equipment, Inc. Date: Copyright 2005.

Erico Guizzo, "Three Engineers, Hundreds of Robots, One Warehouse," IEEE Spectrum. Date: Jul. 2008. Relevant pages: p. 1, paragraphs 1-2 and p. 3, paragraph 3.

"System Solutions for Automated Product Handling" brochure, <www.rowa.de>, Rowa Automatisierungssysteme GmbH, Kelberg, Germany. Date: 2007, Relevant page: p. 4, last paragraph.

"System Solutions for Automated Product Handling" brochure, <www.rowa.de>, Rowa Automatisierungssysteme GmbH, Kelberg, Germany. Date: Sep. 2007, Relevant page: p. 4, last paragraph.

"Rowa Extent" brochure, <www.rowa.de>, Rowa Automatisierungssysteme GmbH, Kelberg, Germany. Date: 2007. Relevant page: p. 2, examples.

"Rowa Scala" brochure, <www.rowa.de>, Rowa Automatisierungssysteme GmbH, Kelberg, Germany. Date: Undated. Relevant page: p. 2, examples.

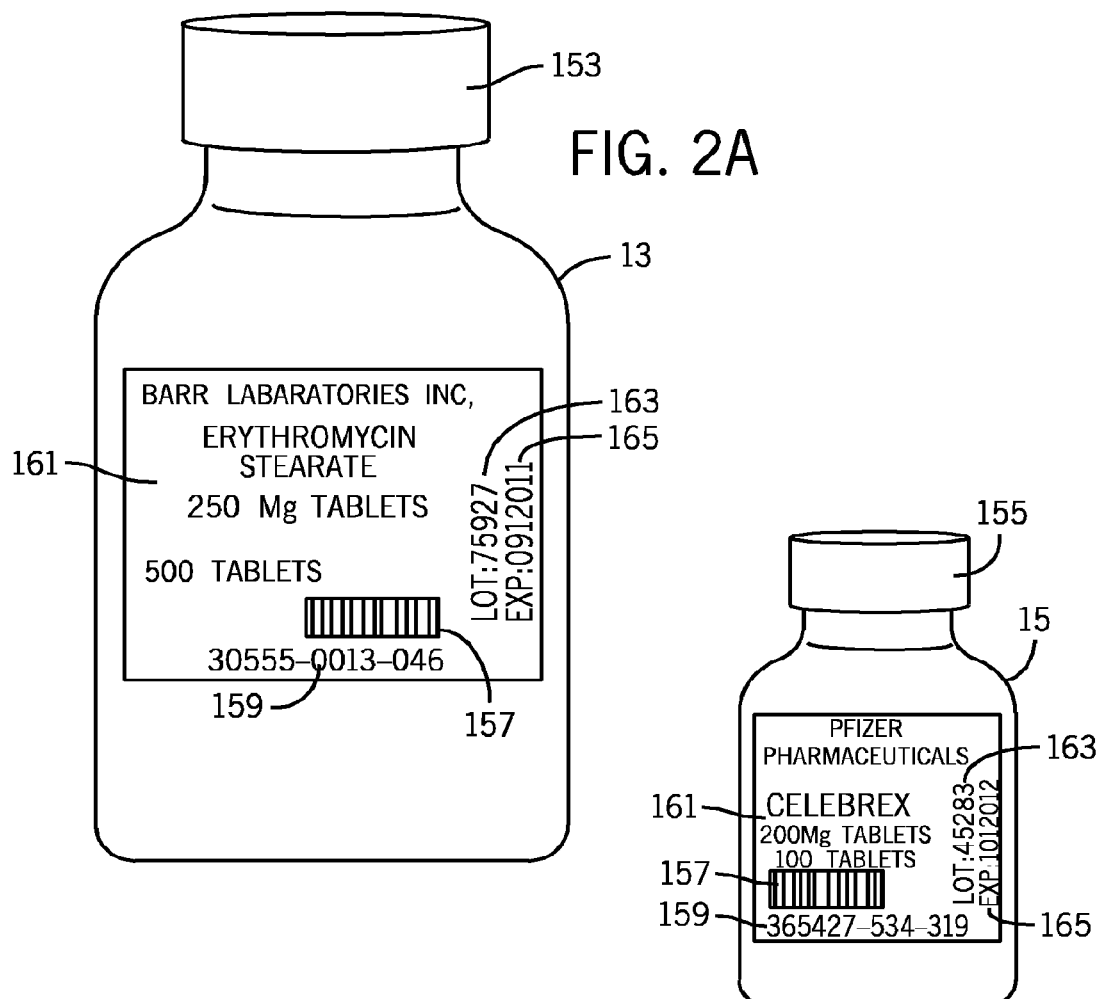
FIG. 2A
FIG. 2B
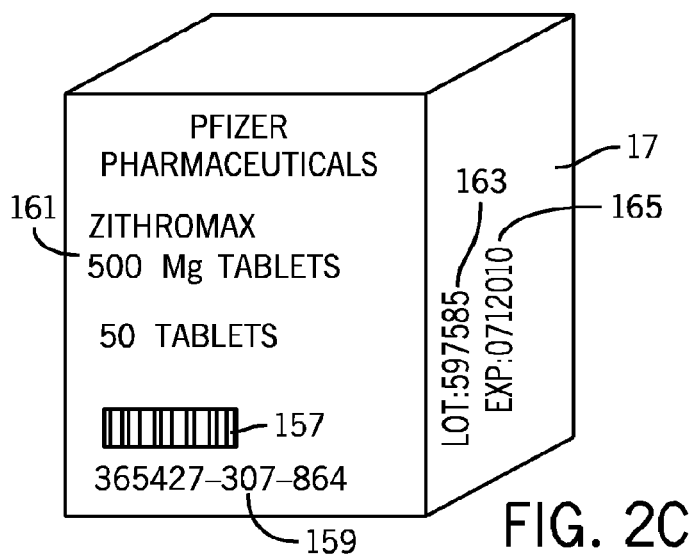
FIG. 2C

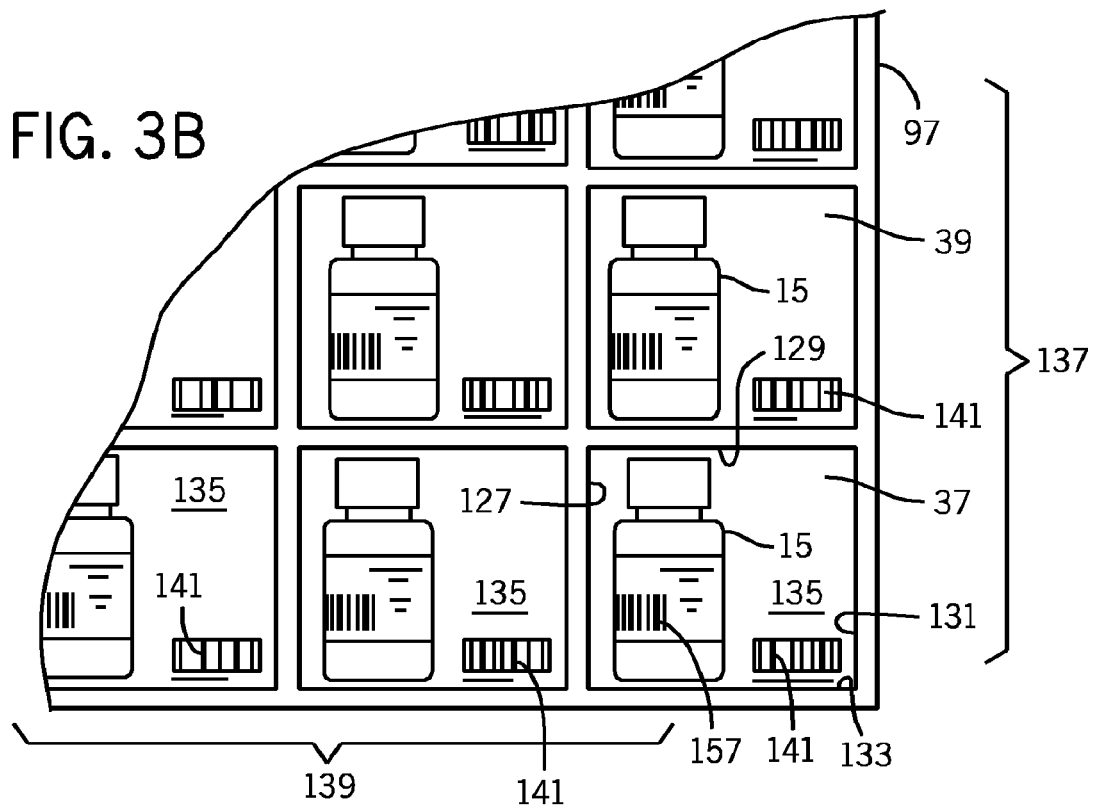
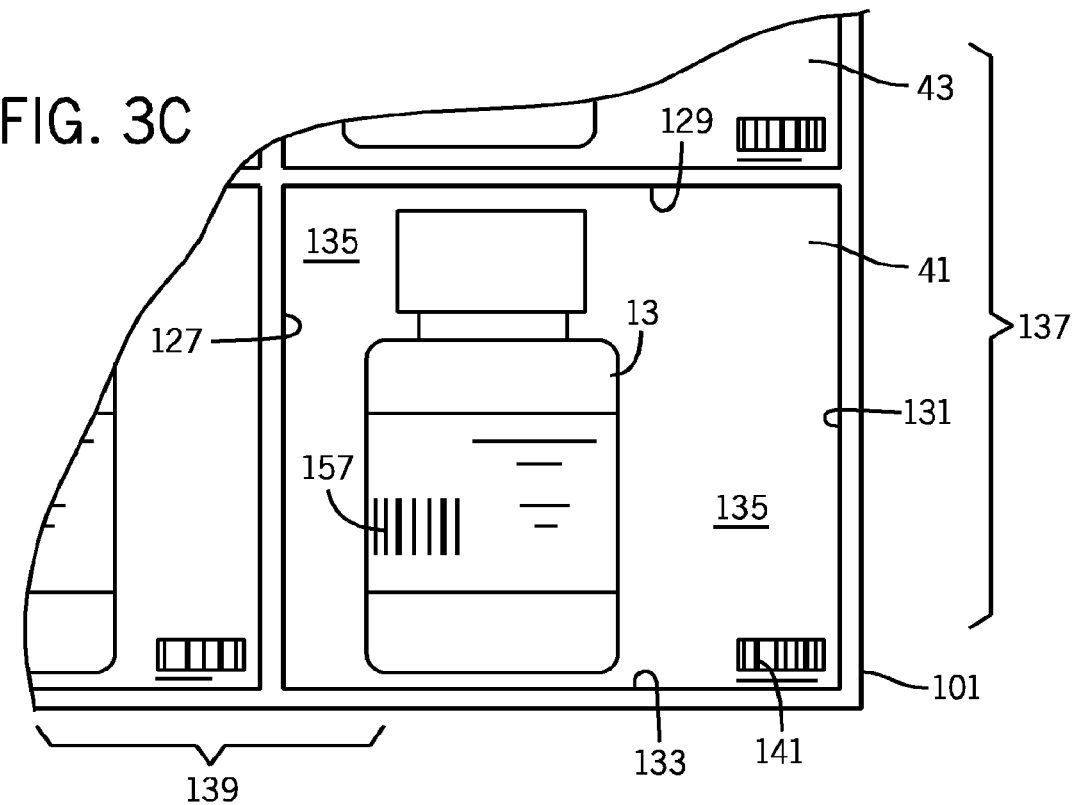

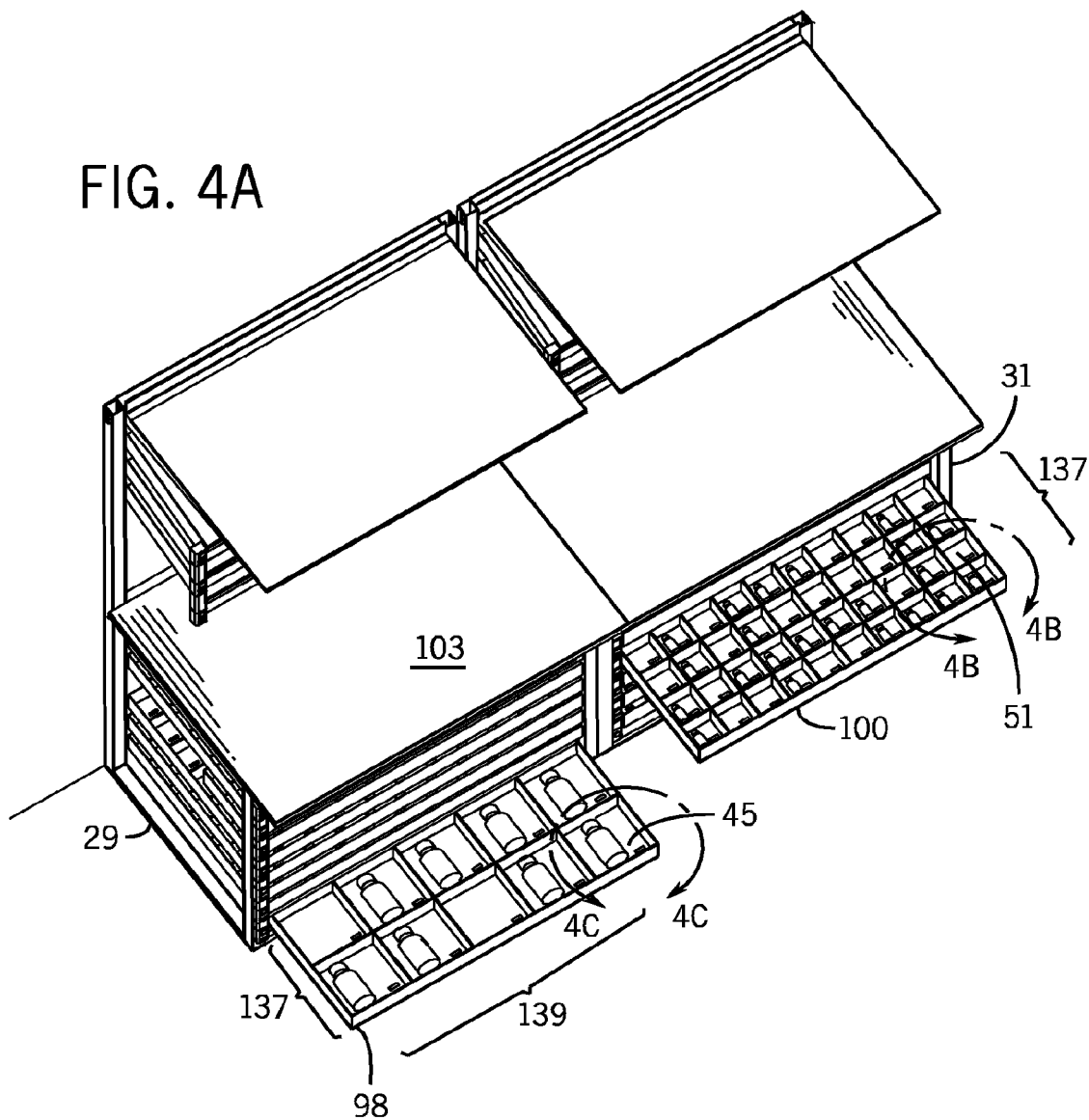

ously before all the of the tablets in the container have been

ADAPTIVE PHARMACEUTICAL PRODUCT MANAGEMENT METHODS AND SYSTEM

RELATED APPLICATION

This application is a continuation of U.S. patent application Ser. No. 12/185,510, filed Apr. 4, 2008, now U.S. Pat. No. 8,165,929, the entire contents of which are incorporated herein by reference.

FIELD

The field relates generally to pharmaceutical product container management and, more particularly, to container management which facilitates prescription order fulfillment as demand for pharmaceutical products changes.

BACKGROUND

Retail, hospital, long-term care and mail-order pharmacies exist to fulfill patient prescription orders. A patient prescription order consists of one or more prescriptions for the patient. In order to fulfill patient prescriptions, the pharmacy will typically stock and manage a large and extensive inventory of pharmaceutical products and other healthcare-related products. Pharmaceutical products include prescription medications, over-the-counter (OTC) medications, nutriceuticals, supplements and other products required to fulfill patient prescriptions or otherwise to meet the needs of customers served by the pharmacy.

Pharmaceutical products are packaged in pharmaceutical product containers. As used herein, pharmaceutical product containers are also referred to simply as "containers." Pharmaceutical product containers may be any suitable type of package and may include, for example, a bottle, a box, a bag or another container type.

Certain pharmaceutical products are routinely stored in bulk-type pharmaceutical product containers. A bulk-type pharmaceutical product container is a container which stores a quantity of a pharmaceutical product in loose, bulk form. The pharmaceutical product is typically in tablet form. As used herein, the term "tablet" is intended to refer to any solid-form pharmaceutical product including tablets, gelcaps, capsules, spheres, multi-angles and the like. The pharmaceutical product stored in a bulk-type pharmaceutical product container can also include powder or liquid-form pharmaceutical product.

Any amount of pharmaceutical product can be stored in a bulk-type pharmaceutical product container. It is common for a bulk-type pharmaceutical product container to store hundreds of tablets or just a few tablets. Tablets are counted out from the bulk-type pharmaceutical product container in order to fulfill a prescription of a prescription order. A bulk-type container may be used many times to fulfill many prescriptions before all the of the tablets in the container have been used and the container is discarded.

Another type of pharmaceutical product container is a unit-dose storage container. A unit-dose container is a prepackaged single dose or course of a pharmaceutical product, such as a week's course of an antibiotic. The entire unit-dose pharmaceutical product container is provided to the patient by the pharmacy. Unit-dose pharmaceutical product containers are provided in various forms such as a pre-loaded clamshell package, a blister package, a box or a bottle. Articles such as syringes and inhalers may also be stocked in unit form.

A pharmacy may stock and manage hundreds, or even thousands, of different pharmaceutical product containers depending on the size and type of pharmacy.

Pharmacies typically maintain their inventory of pharmaceutical products in storage locations which can include, for example, shelves, drawers, cabinets, racks, carousels and refrigerators. Pharmacy storage locations can be automated or non-automated and can be organized and arranged as modular or non-modular storage systems. Each storage location can be further organized, arranged or divided into storage locations at which separate pharmaceutical product containers are located.

A pharmacy will typically include one or more workstation at which pharmacy personnel perform work required to fulfill patient prescriptions. A workstation will typically include a computer terminal and a work surface for collection, preparation and verification of the articles selected to fulfill prescriptions. The pharmacist may stand or sit at the workstation.

In order to fulfill a prescription of a patient prescription order, the pharmacist will typically receive information at the workstation describing the type and amount of pharmaceutical product required to fulfill each prescription. The pharmacist then walks from the workstation to the storage location of the pharmacy at which the pharmaceutical product container for the pharmaceutical product is stored. The pharmacist selects the pharmaceutical product container from its storage location and carries it back to the workstation. If tablet-form pharmaceutical product is required, the pharmacist can count out the required quantity of tablets from the bulk storage container at the workstation. The tablets are placed in a vial or other container which will subsequently be provided to the patient by the pharmacy once fulfillment of the prescription order is complete. Also at the workstation, the pharmacist can perform any other tasks required to fulfill the prescription order such as verification of the selected product containers or placing a patient-specific label on a unit-dose package. Time and effort is required to select and retrieve the pharmaceutical product container from storage and to return any partially-full container back to storage.

Accurate and efficient pharmacy operation is important. Pharmacy personnel must be able to quickly and efficiently locate the storage location for each pharmaceutical product in inventory and must be able to easily select the correct pharmaceutical product container from the storage location. Pharmaceutical products used most frequently should be stored in storage locations which are most easily accessible to the workstation used by pharmacy personnel to fulfill the prescriptions. The storage locations should also be organized and arranged to maximize the available and valuable storage space at the pharmacy.

And, the pharmacy must manage a potentially large and changing inventory of pharmaceutical product containers required to fulfill the prescription orders. Pharmaceutical product containers are constantly being added to, and selected from, the inventory. The inventory of pharmaceutical product containers will include full containers, partially-full containers and may include multiple containers for the same pharmaceutical product but with different quantities, lot numbers and expiration dates.

Complicating pharmaceutical product container inventory management is the fact that the frequency of pharmaceutical product usage changes and is not static. Demand for pharmaceutical products can change, for example, based on factors such as outbreaks of illnesses (e.g., influenza), seasonal demands (e.g., antihistamines and allergy treatments may be used more frequently in the spring and summer), introduction of generics, and introduction or discontinuation of pharmaceutical products. Pharmaceutical product preferences of local physicians can drive changes in demand for certain pharmaceutical products. The pharmaceutical product container inventory should be managed and changed to meet changing patient and customer demand for the pharmaceutical products and so that pharmaceutical products used most frequently are most efficiently and easily accessible to the pharmacy workstation.

A particular problem confronting pharmacy inventory management is the need to efficiently manage the inventory of partially-full pharmaceutical product containers which are picked from storage and potentially placed back into storage many times to fulfill many different prescriptions. A partially-full container is any container which includes fewer than the allotment of tablets or other pharmaceutical product originally contained in the container. Partially-full containers are commonplace in pharmacy inventories because pharmaceutical products are routinely supplied in bulk-type containers which include an amount of tablets (e.g., 100 to 500 or more tablets) which are intended to be used frequently during a long time period before the container is empty and must be discarded.

Several factors may drive the widespread usage of partially-full containers at the pharmacy. One factor is cost. It may cost less for a pharmacy to purchase a large quantity of a pharmaceutical product in a bulk container. Another factor is the generous return policies of most manufacturers. A pharmacy may receive a full or partial refund for a pharmaceutical product, provided the return is made a sufficient amount of time before the expiration date. Thus, there is a clear incentive for the pharmacy to stock partially-full containers because any unused pharmaceutical product may be returned to the manufacturer. As the frequency of usage of pharmaceutical products at the pharmacy changes, these partially-full containers should also be made efficiently and easily accessible to pharmacy personnel at the workstation.

A further need of a pharmacy is the tracking of pharmaceutical product expiration dates so that active pharmaceutical products are provided to the patient and expiring product can be returned to the manufacturer for a refund.

Yet another problem facing a pharmacy is the need to provide theft deterrence. Pharmaceutical products are valuable, and there is a risk that pharmaceutical product containers, or even individual tablets, may be stolen from the pharmacy. Obviously, discouragement of theft is desirable.

There is a need for a pharmacy workflow management system and method which would address some or all of the foregoing pharmacy needs, which would adapt to changes in the frequency of usage of pharmaceutical products, which would make the most frequently used pharmaceutical products most efficiently and easily accessible to the workstation at which the pharmaceutical products are used by pharmacy personnel to fulfill patient prescription orders and which would generally enable the pharmacy to provide a high level of patient care.

SUMMARY

Exemplary methods and systems for adaptive storage of pharmaceutical product containers are described. The methods and system provide for improved pharmacy management by making more frequently used pharmaceutical products more easily accessible to pharmacy personnel working at a pharmacy workstation. The methods and system provide adaptive storage of pharmaceutical products at plural storage locations having rankings based on relative ease-of-accessibility to the pharmacy workstation. As pharmaceutical product usage by the pharmacy changes, the process adapts so that more frequently used pharmaceutical products become stored at the more easily accessible storage locations while pharmaceutical products which are used less frequently become stored at the relatively less accessible storage locations.

In an aspect, the method performed by the system comprises initial placing of plural pharmaceutical product containers into storage locations, each having an ease-of-accessibility ranking. An excess of storage locations is provided to permit adaptive placement of containers into the storage locations. The excess of storage locations provides a type of cache enabling the adaptive movement of the pharmaceutical product containers in inventory. A database record of the storage location of each container is created when each container is placed into storage.

When a prescription is to be fulfilled, the storage location of a pharmaceutical product required for the prescription is automatically visually indicated to a user. The user can then easily pick the container from the indicated storage location. The pharmaceutical product retrieved from the indicated storage location is used to fulfill the prescription and the database is updated, preferably automatically, to indicate use of the product. If there is pharmaceutical product remaining in the container after fulfillment of the prescription, then preferably the container is placed in a restocking bin to await return to storage, although the partially-full container could also be immediately placed back into storage if desired.

When an unopened or partially-full pharmaceutical product container of the pharmaceutical product used to fulfill the prescription is next placed into storage, a determination of a usage frequency ranking for the pharmaceutical product is made and a determination is made of an initial or updated storage location for the container based on the usage frequency ranking. It is preferred that the determination of the usage frequency ranking of the pharmaceutical product is made with a moving-window time period. The determined storage location has an ease-of-accessibility ranking commensurate with the usage frequency ranking of the product.

When the storage location is determined, it is further preferred that the determination is made so that the excess storage locations are distributed throughout the set of storage locations. This is desirable to ensure even distribution of the cache of available storage locations throughout the pharmacy. It is also preferred that distributing the excess storage locations further includes maintaining at least a minimum number of empty storage locations in each of a group of storage locations.

The storage location is automatically visually indicated and the pharmaceutical product container is placed at the indicated updated location.

Preferably, the storage location ease-of-accessibility rankings are based on the relative time required to access each storage location. Exemplary metrics used to determine the time required to access each storage location can include the relative distance of the storage locations from the workstation, relative distance of the storage locations from a drawer front and/or the relative distance of the storage locations from a middle, or mid-point, of a drawer stack. Human factors, such as the necessity to reach and bend to access a storage location, are representative of other metrics that can be used to rank a storage location.

In certain preferred embodiments, the storage locations are grouped into subsets based on storage location size and/or type and the storage location ease-of-accessibility rankings are determined within each subset. This embodiment accommodates containers having different sizes, such as small, medium, or large, and accommodates various types of storage such as drawer-type storage, refrigerated storage and controlled-access storage.

In order to create a database record of the storage location of each pharmaceutical product container, it is preferred that a code on the container is associated with a code of the indicated storage location. It is highly preferred that this associating includes reading a barcode on the container, reading a barcode of the storage location and associating information from the barcodes.

In order to indicate the storage location into which a pharmaceutical product container should be placed to or picked from, it is preferred that the automatically visually indicating of the method performed by the system include energizing a visual indicator to indicate the storage location. The automatically visually indicating may further include energizing at least one lamp indicating the storage location. The lamp may output a color selected from a plurality of colors and the automatically visually indicating may further include energizing the at least one lamp to emit a color associated with a user of a group of concurrent users to direct the user to the storage location.

The methods and system for implementing the methods may include management according to modes. In one mode, the pharmaceutical product rankings are continuously updated so that the storage locations selected for the pharmaceutical products are continuously optimized.

In another mode, the pharmaceutical product rankings are continuously updated but are subject to a time constraint so that the containers are moved only on a periodic basis. This mode is useful to slow the rate at which the storage locations are changed.

In yet another mode, there is provision for anticipated usage frequency of a seasonal product. This mode is particularly useful to ensure that seasonal products are ranked and stored at storage locations commensurate with the in-season and, alternatively, out-of-season usage of the seasonal products.

Other modes involving user-determination of storage locations may be employed. The modes may be used separately or in combination to achieve improved management of pharmaceutical products by the pharmacy.

In another aspect of the method and the system, lot number and/or expiration date tracking is preferably provided. In this embodiment, creating the database record of the storage location of each container further includes creating a database record of the lot number and expiration date of the pharmaceutical product in the container. If the storage locations hold plural containers of the same product, the method may include automatically visually indicating the storage location of the container having an earlier expiration date. Notification may be provided of impending pharmaceutical product expiration. If lot numbers are tracked, identification of the storage location of pharmaceutical product containers of the relevant lot can be provided so that the pharmacy can take appropriate action, such as removing the containers from inventory in the event of a recall.

Theft deterrence may be provided in other aspects of the methods and the system for implementation of the methods. According to this aspect of the methods and system, containers may be secured against theft by placing the containers at a different storage location after each use. The containers are in effect "hidden" among the many storage locations of the system.

BRIEF DESCRIPTION OF THE DRAWINGS

Exemplary methods and systems for adaptive storage of pharmaceutical product containers at a pharmacy may be understood by reference to the following description taken in conjunction with the accompanying drawings, in which like reference numerals identify like elements throughout the different views. The drawings are not necessarily to scale, emphasis instead being placed upon illustrating the principles of the invention. In the accompanying drawings:

FIGS. 2A, 2B and 2C are exemplary pharmaceutical product containers;

FIG. 3B is a detail view taken along detail section 3B-3B of FIG. 3A showing plural storage locations of a first size;

FIG. 3C is a detail view taken along detail section 3C-3C of FIG. 3A showing plural storage locations of a second size;

FIG. 4A is a top perspective view of a further drawer-type storage module including plural storage locations;

FIGS. 9A and 9B illustrate container placement, and FIGS. 9C-9D illustrate container picking and prescription fulfillment.

DETAILED DESCRIPTION

Figure 1:
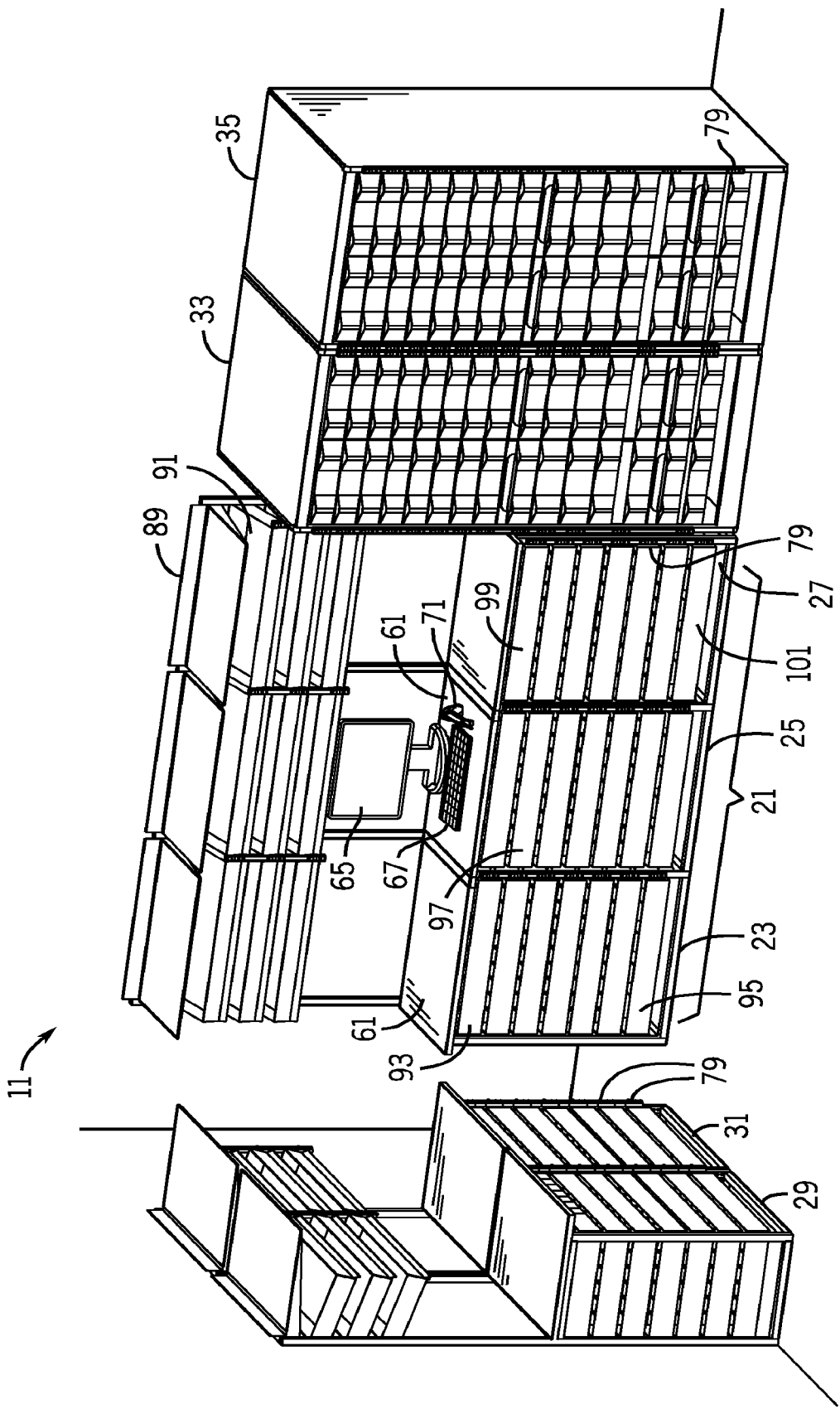
FIG. 1 is a perspective view of an exemplary pharmacy, including a workstation and storage modules.

Exemplary methods and systems 11 for adaptive storage of pharmaceutical product containers, such as containers 13, 15, 17, 18, 19 at a pharmacy, will first be described with respect to FIGS. 1-8. As used herein, "adaptive" means or refers to having the capability of adjusting to changes in conditions. System 11 adapts to actual and anticipated changes in pharmaceutical product usage frequency.

Referring first to FIGS. 1-8, a system 11 for adaptive storage of pharmaceutical products (e.g., containers 13-19) used to fulfill patient prescription orders by a pharmacy includes a workstation 21 and storage modules 23, 25, 27, 29, 31, 33, 35 with plural storage locations, examples of which 37, 39, 41, 43, 45, 47, 49, 51, 53, 55, 57, 59 are illustrated in FIGS. 3A-3C, 4A-4C, and 5B. The pharmacy inventory of pharmaceutical product containers (e.g., containers 13-19) is stored among the storage locations (e.g., locations 37-59).

In the example, the storage locations (e.g., locations 37-59) are fixed-position storage locations. A fixed-position storage location means or refers to a storage location with a unique address and position within system 11 and which is not transported about the pharmacy with the pharmaceutical product container (e.g., container 13, 15, 17, 18, 19). A container (e.g., one of containers 13-19) of the appropriate size may be stored at each such storage location (e.g., locations 37-59).

The storage locations (e.g., locations 37-59) are organized in a hierarchy with each storage location having a ranking first-to-last based on the relative ease of access of each storage location to workstation 21. "Ease of access" means or refers to an assessment of the ease and/or efficiency with which a storage location is reached or accessed by pharmacy personnel. The assessment can be made based on a variety of factors described herein. Such a ranking of the storage locations (e.g., locations 37-59) enables system 11 to direct storage of the containers (e.g., containers 13-19) for the most frequently-used pharmaceutical products to the storage locations (e.g., locations 37-59) most easily accessible to the workstation 21. Rules for distributing of the containers (e.g., containers 13-19) among the storage locations (e.g., locations 37-59) are described below.

Workstation 21 represents a sort of pharmacy "hub" or pharmacy "center" around which modules 23-35 and the ranked storage locations (e.g., locations 37-59) are positioned and arranged. It is an important object of system 11 that full and partially-full pharmaceutical product containers (e.g., containers 13-19) for the most-frequently used pharmaceutical products are stored among the ranked storage locations (e.g., locations 37-59) most easily and efficiently accessible to the workstation 21. Such positioning makes it possible to locate an unsealed, partially-full pharmaceutical product container (e.g., container 13-19) for a popular pharmaceutical product at a storage location which is easily accessible to pharmacy personnel at the workstation 21. Such an arrangement makes it easier and more efficient for pharmacy personnel working at workstation 21 to place pharmaceutical product containers (e.g., containers 13-19) into the storage locations (e.g., locations 37-59) and to pick pharmaceutical product containers (e.g., containers 13-19) from such storage locations to prepare each patient's prescription order at workstation 21 or to place containers back into the storage locations.

As will be described, system 11 adapts to real-time and anticipated changes in pharmaceutical product usage frequency and directs placement of full and partially-full pharmaceutical product containers (e.g., containers 13-19) to a storage location (e.g., locations 37-59) based on usage frequency each time the pharmaceutical product container (e.g., containers 13-19) is placed into storage. As used herein, "usage frequency" means or refers to the number of times a particular product is accessed to fulfill prescriptions within a given period of time.

Workstation 21 is provided for the use of pharmacy personnel to perform prescription order fulfillment and other tasks. A "user" of workstation 21 may be any of the pharmacy personnel including a registered pharmacist, a pharmacy technician, a restocking clerk, or any other authorized user. In the example, workstation 21 may also be used to perform a variety of tasks including intake of new pharmaceutical product containers (e.g., containers 13-19) into inventory and general inventory management, such as removal from inventory of pharmaceutical product containers with expired pharmaceutical products.

Figure 8:
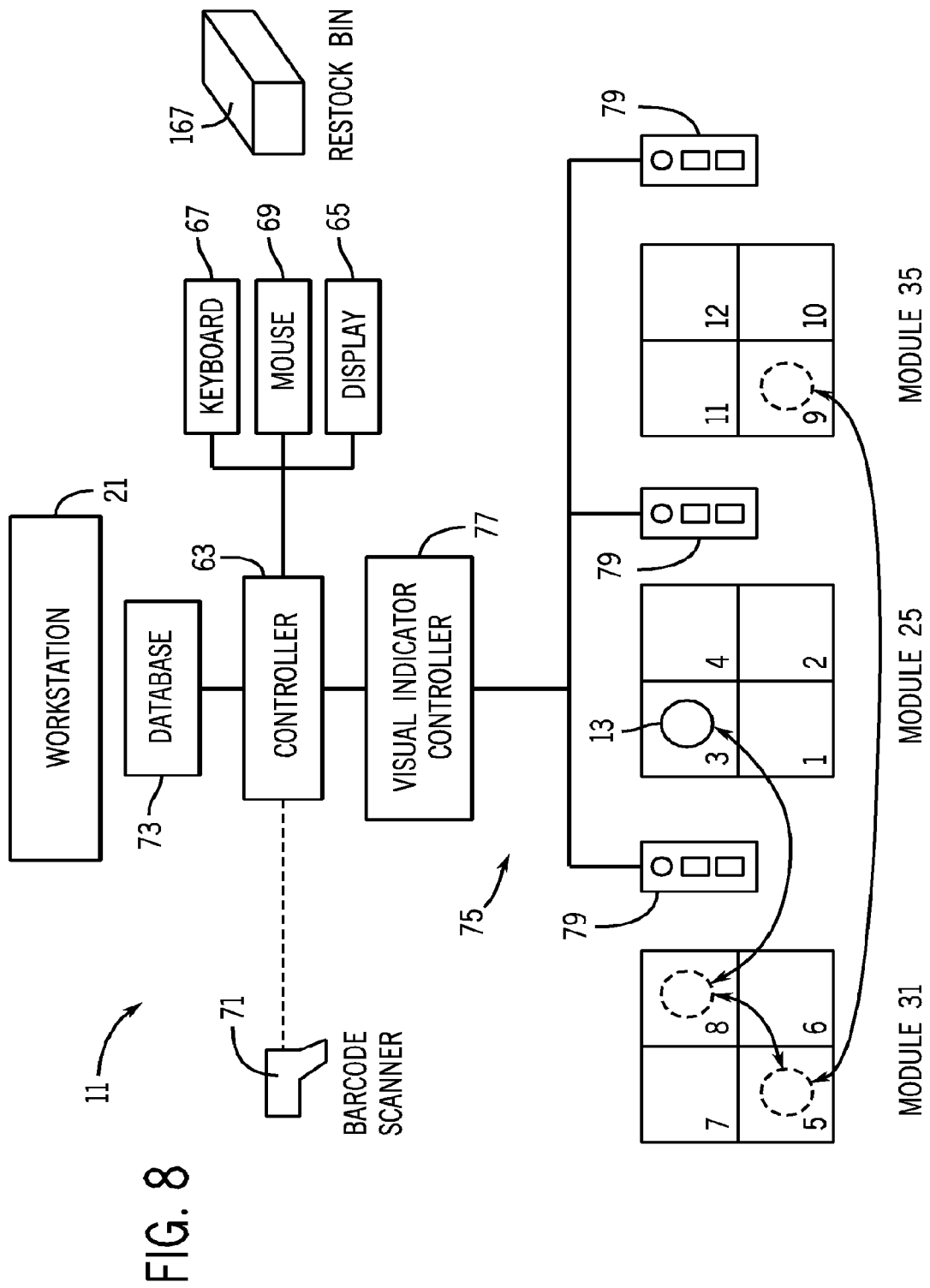
FIG. 8 is a schematic illustration of an adaptive pharmaceutical product storage system.

In the example, workstation 21 includes a worksurface 61 at which patient prescription orders may be prepared by a user. Referring to FIG. 8, workstation 21 is provided with a controller 63. Also provided are a video display 65, a keyboard 67, a mouse 69 and a code reader in the form of a barcode reader 71 each operatively connected to controller 63. Display 65 may be a touch-screen type display 65 with a QWERTY-type keypad emulation display image which permits a user to input information to controller 63 by touching display 65 proximate a displayed control button or information field or by keying in information with the keypad. Barcode reader 71 is an off-the-shelf barcode scanner provided to output barcode information to controller 63 each time a container (e.g., containers 13-19) is picked or placed, enabling accurate tracking of each container (e.g., containers 13-19) in inventory as described herein.

Controller 63 may, for example, consist of an off-the-shelf personal computer (PC) or plural operably-connected PCs. For example, controller 63 may consist of one or more central processing unit (CPU). In this example, a PC-type CPU would include non-volatile memory holding a database 73 having a record of the unique address of each storage location (e.g., locations 37-59) and the ease-of-accessibility ranking of each storage location. Database 73 may include the number of storage locations (e.g., locations 37-59) within system 11 and the size (e.g., small, medium, or large) and type of each storage location. For example, storage location types may include general storage locations, refrigerated storage locations or controlled-access storage locations. A PC-type CPU used to instantiate controller 63 could provide a user interface with display 65, keyboard 67, mouse 69 and barcode reader 71 enabling user access to controller 63.

Storage locations may be grouped into subsets by storage location size and/or type. Therefore, there may be a group of storage locations designated for holding large-size containers, for holding medium-size containers, or for holding small-size containers. Also for example, there may be a group of storage locations designated for holding perishable products requiring refrigeration and a group of storage locations designated for narcotic products requiring controlled access.

Database 73 is capable of associating any pharmaceutical product container (e.g., containers 13-19) with any storage location (e.g., locations 37-59). This includes creating a record of the storage location into which a container (e.g., containers 13-19) is placed and subsequently updating that record with the updated storage location when the container (e.g., containers 13-19) is placed back into storage.

Controller 63 may also directly or indirectly control operation of an Optical Positioning System (OPS) 75 which is a pick-to-light/place-to light visual indicator system 75 provided to indicate to a user the storage location (e.g., location 37-59) at which each pharmaceutical product container (e.g., containers 13-19) should be placed or picked. In the example, OPS 75 consists of controller 63, visual indicator controller 77 and a visual indicator 79 adjacent one or more storage locations (e.g., locations 37-59) as described herein. Any number of visual indicators 79 may be used depending on the quantity and arrangement of the storage locations (e.g., location 37-59) implemented by the pharmacy.

As illustrated schematically in FIG. 8, controller 63 is operatively connected to visual indicator controller 77 through electronic means, such as a serial cable. Visual indicator controller 77 is operatively connected to each visual indicator 79 of OPS 75 via cables or any other suitable means. After receiving a signal from controller 63, visual indicator controller 77 is operative to activate the relevant visual indicator 79 as described herein. OPS system 75 and its use is described in more detail below. Visual indicator controller 77 may be a device such as a model TW2208 Ethernet Small Controller available from Lightning Pick Technologies of Germantown, Wis.

The physical structure of modules 23-27 comprising workstation 21 will now be described in connection with FIGS. 1 and 3A-3C. Modules 23-27 are identical to modules 29-31 illustrated in FIGS. 1 and 4A-4C. For convenience and brevity, the physical structure of module 27 of workstation 21 is described, it being understood that the description of module 27 is applicable to modules 25-31.

Module 27 includes a base 80, vertical columns 81, 83, 85, 87 and a shelving unit 89 supported on rear columns 85, 87. Shelving unit 89 includes plural shelves for holding articles and things used by the pharmacy. One shelf of shelving unit 89 is designated by reference number 91. Shelving unit 89 shelves (e.g., shelf 91) could provide fixed-position storage locations for containers such as containers 13-19, if desired. For example, shelf 91 may be a "speed shelf" in which like pharmaceutical product containers are stored in columns on a sloped shelf and are moved to the shelf front by gravity after removal of the front container in the column of like containers.

Figure 3A:
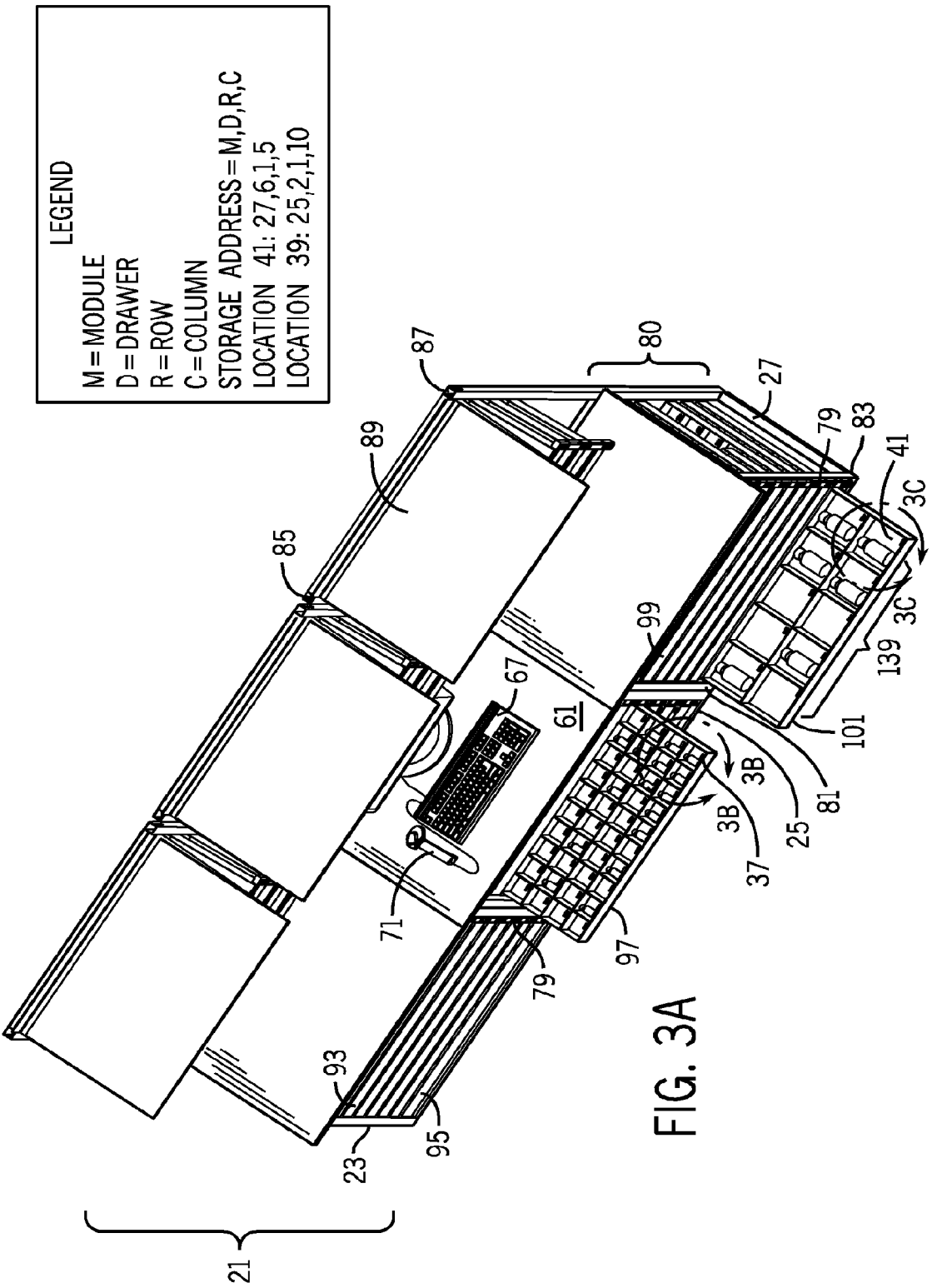
FIG. 3A is a top perspective view of a drawer-type storage module including plural storage locations.
Figure 4B:
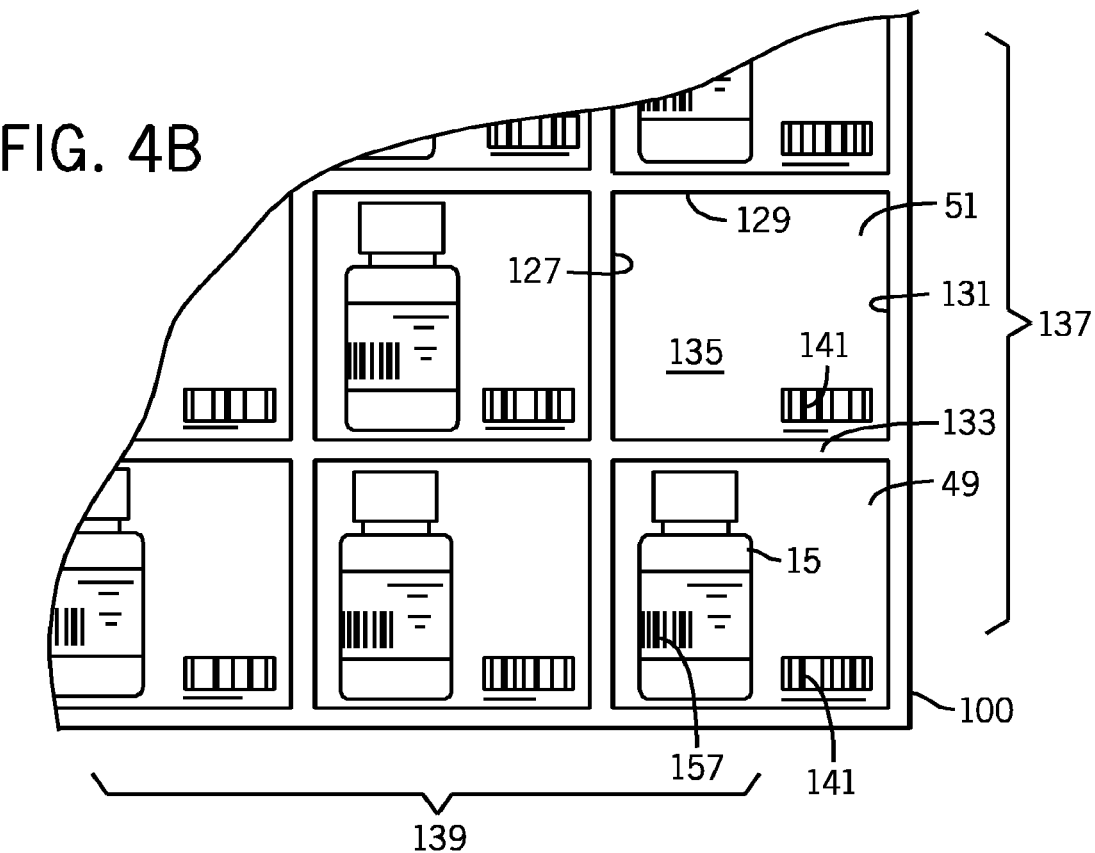
FIG. 4B is a detail view taken along detail section 4B-4B of FIG. 4A showing plural storage locations of the first size.
Figure 4C:
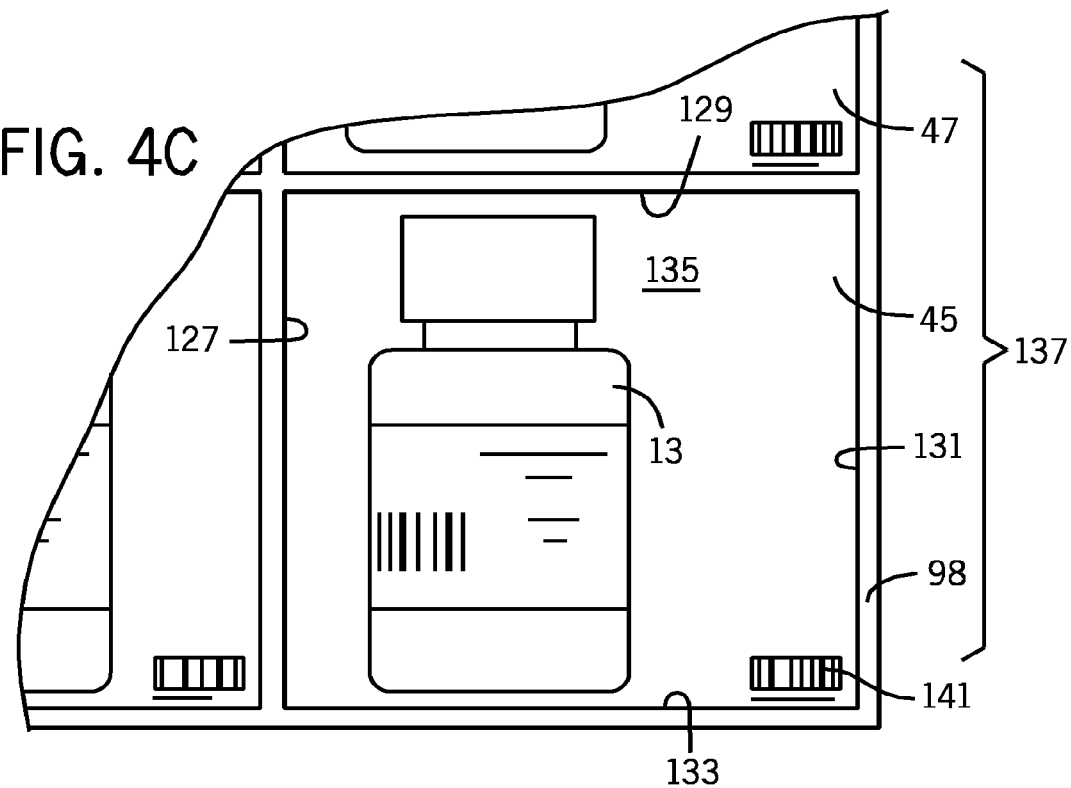
FIG. 4C is a detail view taken along detail section 4C-4C of FIG. 4A showing plural storage locations of a second size.

Referring to FIGS. 3A and 4A, base 80 includes plural drawers, two of which are identified by reference numbers 99, 101. Additional drawers on other modules 23, 25, 29, 31 are designated by reference numbers 93, 95, 97, 98 and 100. Each drawer 93-101 is mounted on a slide (not shown) which enables each drawer to be moved into the respective base (e.g., base 80) and to be moved in and out between a position in which the drawer (e.g., drawer 101) is retracted into its base (e.g., base 80) and alternatively extended out of the respective base (e.g., base 80) as illustrated in FIGS. 3A and 4A to permit user-access to the fixed-position storage locations (e.g., locations 37-59) located therein for placement or picking of pharmaceutical product containers (e.g., containers 13-19).

Worksurface 61 of workstation 21 is supported on base 80 and the like bases of modules 25-27. Worksurface 103 is supported on the respective bases of modules 29-31. Positioning modules 23-27 and 29-31 side-by-side as shown in FIGS. 1, 3A and 4A permits each worksurface 61, 103 to extend across all adjacent modules 23-27 and 29-31, providing convenient places for a user to perform tasks such as counting and verifying each pharmaceutical product required to fulfill patient prescriptions.

Figure 5A:
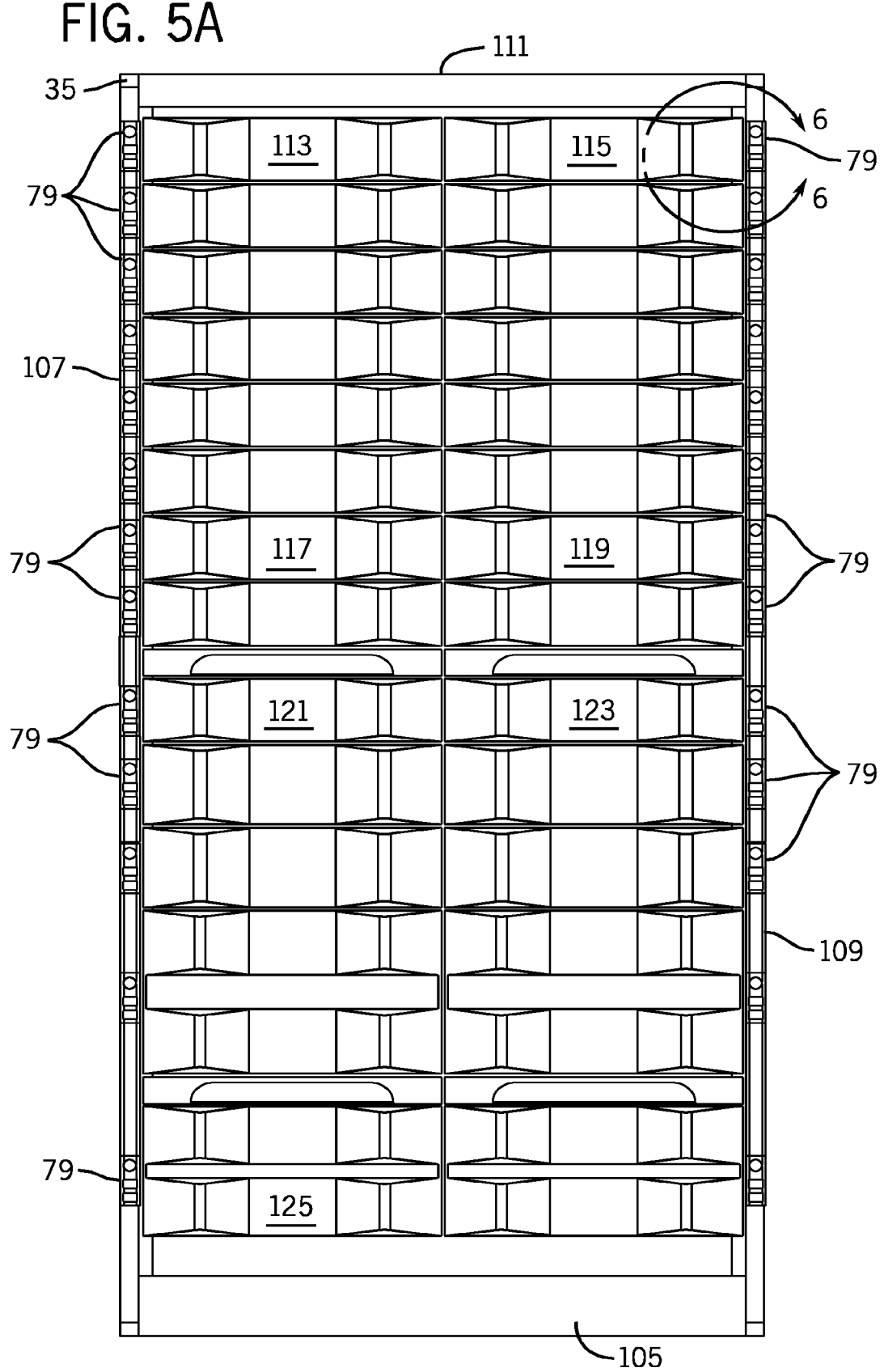
FIG. 5A is a front elevation view of a drawer-type storage module including plural storage locations.
Figure 5B:
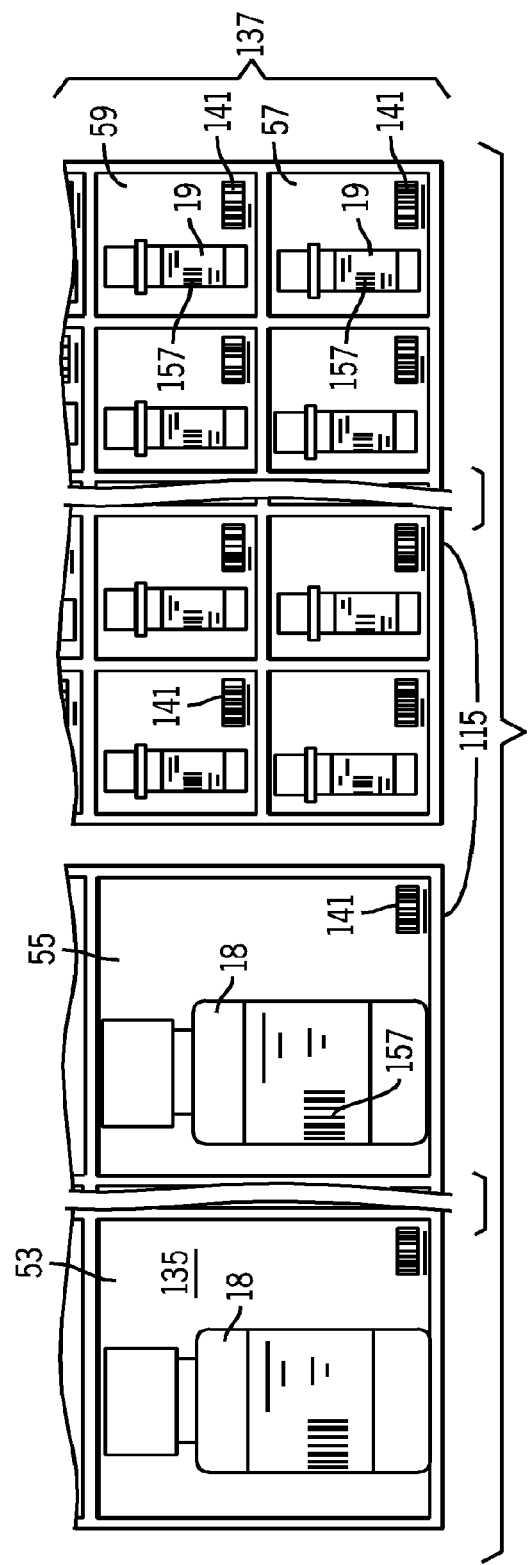
FIG. 5B is an enlarged view of a drawer pulled out from the storage module of FIG. 5A including plural storage locations of the first size and a third size.
Figure 6:
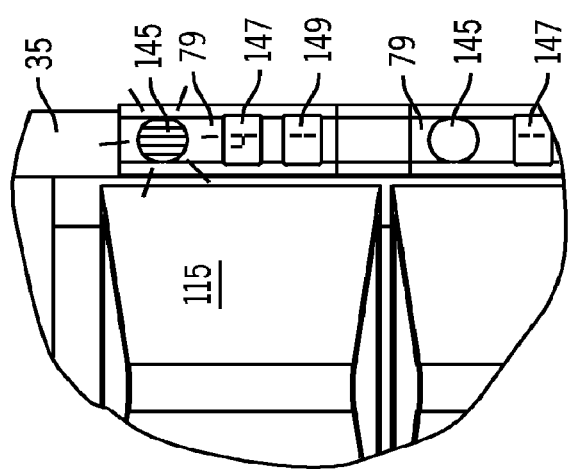
FIG. 6 is a detail view taken along detail section 6-6 of FIG. 5A showing a visual indicator.

Referring next to FIGS. 1, 5A and 5B, the physical structure of exemplary modules 33 and 35 will next be described. Modules 33 and 35 are identical in the example. For convenience and brevity, the structure of module 35 is described, it being understood that the description of module 35 is applicable to module 33.

Module 35 includes a base 105, side walls 107, 109, a top wall 111 and an unshown rear wall forming a cabinet-type enclosure. Module 35 includes plural drawers, two of which are indicated by reference numbers 113 and 115. Additional drawers of module 35 are designated by reference numbers 117, 119, 121, 123 and 125. Each drawer (e.g., drawers 113-125) is mounted on a slide (not shown) which enables each drawer to be moved in and out between a position in which the drawer (e.g., drawer 113-125) is retracted into module 35 and, alternatively, extended out of the module 35 as illustrated in FIGS. 5A and 5B to permit user-access to the fixed-position storage locations (e.g., locations 53-59) therein for placement or picking of pharmaceutical product containers (e.g., containers 13-19).

In the example, each fixed-position storage location (e.g., locations 37-59) in each drawer (e.g., drawers 93-101 and 113-125) is defined by side walls 127, 129, 131, 133 and bottom wall 135. The result in the example is a grid-like arrangement of fixed-position storage locations (e.g., locations 37-59) arranged in rows 137 and columns 139.

In the example, walls 127-133 of each storage location (e.g., locations 37-59) define three different sizes of storage locations (e.g., locations 37-59) which are referred to herein for simplicity as either "small," "medium," or "large" storage locations. Each size may be treated as a separate storage location type and subset. In the example, small-size storage locations are indicated by reference numbers 37, 39, 49, 51, 57 and 59, medium-size storage locations are indicated by reference numbers 53, 55, and large-size storage locations are indicated by reference numbers 41, 43, 45, and 47. In the example, the large-size storage locations 41-47 have a volumetric space which is about four times greater than the volumetric space of small-size storage locations 37, 39, 49, 51, 57, 59. While three sizes are shown, it should be understood that any number of different size locations may be provided.

In the example, each storage location (e.g., locations 37-59) has a unique address within system 11. In the example, the address is based on its: (1) module identifier (herein the reference numbers 23-35 are used as the identifier), (2) drawer identifier (herein based on the number of drawers in a module), (3) row number (herein based on the number of rows in a drawer), and (4) column number (herein based on the number of columns in a drawer). As indicated in the Legend of FIG. 3A, the unique address for storage location 41 is 27, 6, 1, 5 meaning module 27, drawer 6 (6th from the top), row 1, column 5. The Legend of FIG. 4A states that the unique address of storage location 51 is 31, 2, 2, 10 meaning module 31, drawer 2 (2nd from the top), row 2, column 10. Each other storage location (e.g., locations 37-59) has a unique address determined in the same manner. Any system of unique storage location identification can be implemented.

Referring to FIGS. 3B, 3C, 4B, 4C and 5B, the unique address of each storage location (e.g., locations 37-59) is embedded in a machine-readable code, preferably a barcode 141, affixed to each storage location (e.g., locations 37-59) bottom wall 135. The storage location barcode 141 is scanned with barcode scanner 71 during each occurrence of placing a container (e.g., container 13-19) into the storage location (e.g., locations 37-59) for purposes of updating database 73 to accurately indicate the storage location of each pharmaceutical product container (e.g., containers 13-19) in inventory as described in more detail below.

Each storage location (e.g., locations 37-59) is ranked within system 11 based on its ease-of-accessibility to workstation 21 relative to each other storage location in a set or subset of a group of like storage locations (e.g., large-size storage locations or refrigerated storage locations). Ease-of-accessibility is related most directly to the amount of time that is required to access the storage location from workstation 21. Other considerations, such human factors (e.g., bending and reaching to access a storage location), may also be utilized to determine the ranking although the impact of these other factors may be included in the time-to-access metric.

Accordingly, ease-of-accessibility metrics can be based on the linear distance (horizontal or vertical) of the storage location (e.g., locations 37-59) from the workstation 21. Storage locations closer to the workstation require less time to access and have a correspondingly more favorable ranking. According to a linear distance ranking metric, storage locations in modules 23-27 would have more favorable rankings than storage locations in modules 29-35 because storage locations in modules 23-27 are located at workstation 21 whereas storage locations in modules 29-35 are spaced from workstation 21.

By way of further example, ease-of-accessibility can be based on relative drawer location (e.g., drawers 93-101, 113-125). According to this ranking metric, a drawer located toward the cabinet middle or mid-point (e.g., drawer 117, 119, 121 or 123) which is easily opened by a user may be deemed more easily accessible than either a drawer toward the cabinet top wall 111 (e.g., drawer 113 or 115) which may require use of a step ladder to access. Such a middle drawer may be more easily accessible from a human factors standpoint because the user does not have to bend down as would be the case when accessing a drawer toward the cabinet base 105 (e.g., drawer 125). Similarly, storage locations in an upper drawer (e.g., drawer 97) of module 25 could have a more favorable ranking than storage locations in a lower drawer (e.g., drawer 101) of module 27 because of the relatively greater ease with which storage locations in drawer 97 could be accessed by a user standing or seated at workstation 21.

By way of yet another example, ease-of-accessibility can be based on row and column locations within a single drawer (e.g., drawer 100). According to this ranking metric, storage locations in rows 137 closer to the drawer front can be accessed more rapidly than storage locations in rows 137 closer to the drawer rear. From a human factors standpoint, a row in the rear of the drawer may be particularly inconvenient because the user must reach to the rear of the drawer. This could make rear rows of a bottom drawer (e.g., drawer 125) particularly inaccessible resulting in a low ranking Combinations of any and all ranking metric methodologies may be implemented.

The entire set or subset of storage locations (e.g., locations 37-59) available at the pharmacy for storage of pharmaceutical product containers (e.g., containers 13-19) is stored in database 73 maintained in non-volatile memory of controller 63. This stored information includes the address and ranking of each storage location (e.g., locations 37-59). Separate rankings may stored in database 73 for locations within a subset of storage locations of a particular type or size.

Therefore, if system 11 includes a total set of 10,000 storage locations (e.g., locations 37-59), each storage location is ranked from 1 to 10,000 based on ease-of-accessibility to workstation 21, and the rankings are associated with the unique addresses and barcodes 141 for the locations. If system 11 were to include a subset of 8,000 storage locations of one size (e.g., small size) and further subsets of 1,000 storage locations of a second size (e.g., large size) and 1,000 storage locations of a third size (e.g., medium size), then each storage location within such subsets may be ranked from 1 to 8,000 or 1 to 1,000 , respectively. Aspects of the storage location ranking may be somewhat subjective because, for example, abutting storage locations in the same drawer are each likely to be as easily accessible to the workstation 21 as the other.

It may be desirable to provide yet additional organizational hierarchical levels, for example, grouping storage locations (e.g., locations 37-59) into subsets based on "zones" for storage of pharmaceutical products with similar frequency of usage or some other characteristic. Each zone subset could be designated based on pharmacy-selected metrics. For example, each zone could be designated based on the linear distance (e.g., close or far) of the zone from workstation 21. Storage locations (e.g., locations 37-59) within each zone subset could be ranked first-to-last based on ease-of accessibility to workstation 21 within the zone subset. For example, modules 23-27 could represent an A-mover zone because such modules abut to comprise workstation 21. Modules 29-31 could represent a B-mover zone because modules 29-31 are spaced from workstation 21 as illustrated in FIG. 1. Modules 33-35 could represent a C-mover zone.

An advantage of the exemplary system 11 is that it is not necessary to segregate like pharmaceutical product containers (e.g., containers 13-19) and to store like containers together, as on a shelf. Subject to the need to have a greater number of storage locations than containers in order for the adaptive behavior of system 11 to occur, system 11 provides for "dense" storage which efficiently utilizes available and valuable pharmacy storage space. Therefore, if there are more pharmaceutical product containers of one type than another in stock at any particular time, storage space reserved for the less abundant container is not wasted as would be the case with segregated storage. As described below, the excess number of storage locations provides a cache or buffer for the adaptive inventory movement to occur as described herein.

Referring now to FIGS. 1, 3A, 4A, 5A, 6, 7A-7C and 8, OPS system 75 assists the user in rapidly and accurately identifying the storage location (e.g., locations 37-59) into which each pharmaceutical product container (e.g., container 13-19) is to be placed, picked from or returned to after fulfillment of a patient prescription. OPS system 75 controlled by controller 63 and visual indicator controller 77 consists of visual indicator 79 adjacent each drawer (e.g., drawers 93-101, 113-125). Each visual indicator 79 is preferably identical in structure and operation and is connected to visual indicator controller 77 via a cable or other suitable connection as previously described. Also as previously described, OPS system 75 includes a sufficient number of visual indicators 79 to indicate the location of each storage location (e.g., locations 37-59).

Figure 7A:
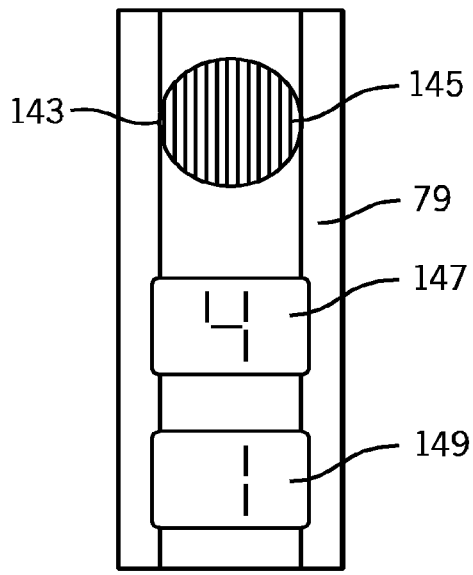
FIGS. 7A, 7B and 7C show a single visual indicator in three different states, each state including output of a different color light.
Figure 7B:
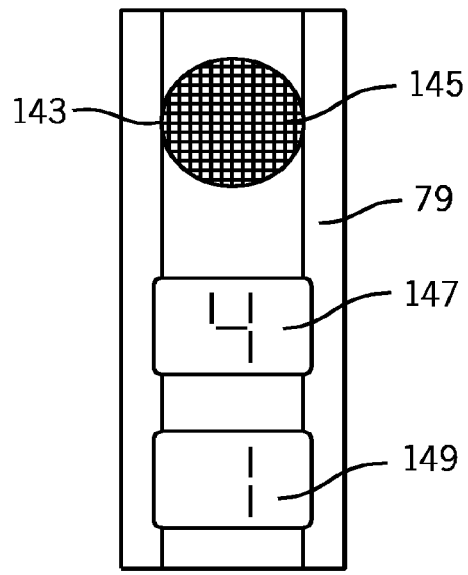
Figure 7C:
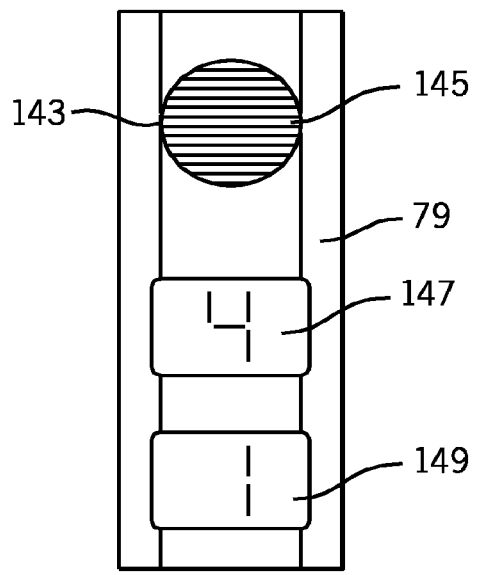

Referring to FIGS. 7A-7C, each visual indicator 79 includes a housing 143, a lamp 145 and a pair of digital numeric displays 147, 149. Energizing of lamp 145 by controller 77 indicates the drawer (e.g., drawers 93-101, 113-125) in which the storage location (e.g., locations 37-59) is located. Display 147 is activated by controller 77 to indicate the row 137 and display 149 is activated by controller 77 to indicate the column 139 of the storage location (e.g., locations 37-59). In the examples of FIGS. 7A-7C, the user is being prompted to pick or place from the storage location (e.g., locations 37-59) at row 4, column 1 of the indicated drawer (e.g., drawers 93-101, 113-125).

Optionally, lamp 145 may be configured to facilitate simultaneous use of system 11 by plural users. In such embodiments, lamp 145 may be a multi-colored light emitting diode (LED). FIGS. 7A-7C alternatively show lamp 145 emitting red, yellow or blue colors. One color is associated with each currently-active user. A single user is directed to the storage location (e.g., locations 37-59) indicated by the color of the lamp 145 associated with the user, thereby avoiding any confusion about which user should access a particular storage location (e.g., locations 37-59).

Non-limiting, exemplary pharmaceutical product containers which may be stored within the storage locations (e.g., locations 37-59) are now described in connection with FIGS. 2A-2C and FIGS. 3B, 3C, 4B, 4C and 5B. Container types other than shown in the figures may be stored in pharmacy inventories. Examples are clamshells, bags and blister packages. Containers 13, 15, 18 and 19 are lightweight plastic pharmaceutical-product-containing bottles, and container 17 is a box. Each container identified by reference number 13 may be characterized as a "large" bulk-storage-type container which may have volume of about 1,000 cm$^3$ and may hold 500 tablets when originally loaded. Containers identified by reference numbers 15, 17 and 19 may be characterized as a "small" bulk-storage-type containers while container 18 is a "medium" container. Container 15 may have a volume of about 250 cm$^3$ and may hold 100 tablets. Box 17 contains antibiotic tablets but could hold other pharmaceutical products such as an inhaler or syringe. Container 13 is approximately four times larger than container 15 on a volumetric basis. Container 18 has a size between that of containers 13 and 15.

Containers 13, 15, 17, 18, 19 are provided by the manufacturer with a safety seal (not shown) over a container opening, and a replaceable closure 153, 155 is secured over the sealed opening. Closure 153, 155 may be a threaded cap which meshes with threads on the neck of each container 13, 15. Closure 153, 155 is removed from the respective container 13, 15 by a user to pour tablets from the container 13, 15 and is replaced by the user to place a partially-full container back into storage. Partially-full containers are commonplace in pharmacy inventories because pharmaceutical products are routinely supplied in bulk-type containers which include a large number of tablets (e.g., such as 500 count container 13) and are intended to be used multiple times, potentially over a long time period before expiration of the pharmaceutical product in the container.

Referring further to FIGS. 2A-2C, each pharmaceutical product container 13-19 is provided with a unique machine-readable code, preferably in the form of a barcode 157. The barcode 141 of a storage location (e.g., location 37-59) and the container barcode 157 are each scanned each time the container (e.g., 13-19) is placed into a storage location (e.g., locations 37-59). Container barcode 157 is also scanned during each occurrence of picking the container (e.g., container 13-19) from its storage location (e.g., locations 37-59).

The unique barcode 157 of the container (e.g., 13-19) is associated in database 73 with the unique address of the storage location (e.g., locations 37-59) into which the container is placed. When each container (e.g., containers 13-19) is picked, scanning of barcode 157 updates database 73 to indicate that the container (e.g, container 13-19) has been removed from storage for purposes of fulfillment of a prescription. The scanning also indicates that the storage location is available to receive another container as part of the adaptive behavior of system 11. Controller 63, therefore, maintains an accurate real-time record of the location of each container (e.g., container 13-19) in inventory and the location of each available storage location in the cache of available storage locations.

Container barcode 157 is typically a Universal Product Code (UPC) barcode but may be of any barcode type. Barcode 157 provides information uniquely identifying the pharmaceutical product in container 13-19. Typically, the 10-digit National Drug Code (NDC) for the prescription pharmaceutical product is embedded in a UPC-type barcode 157 and provides unique identification for the pharmaceutical product and container 13-17. Human-readable information 159 adjacent each barcode 157 on containers 13-17 shows the 10-digit NDC embedded in barcode 157 for the pharmaceutical product.

Other types of machine-readable codes can be provided on, or associated with, containers 13-19. For example, each container 13-19 could include a radio frequency identification (RFID) tag in place of or in combination with a respective barcode 157.

Other information provided on each container 13-19 typically includes manufacturer name, pharmaceutical product type, strength and quantity 161, a lot number 163 and an expiration date 165. Lot number 163 identifies the production batch and date of manufacture, and the expiration date 165 is the date by which the pharmaceutical product should no longer be used. System 11 may be utilized to track expiration dates to permit the pharmacy to return expiring pharmaceutical products to the manufacturer for a refund as described herein.

A strength of system 11 is that the structure, arrangement and number of modules 23-35, drawers (e.g., drawers 93-101, 113-125), rows 137, columns 139 and storage locations (e.g., locations 37-59) of system 11 can be configured, arranged, scaled and changed over time to meet the unique and evolving needs of each different pharmacy. These needs can include increased or decreased prescription-order fulfillment demand at the pharmacy, increased or decreased demand for pharmaceutical product container storage and budgetary considerations of the pharmacy.

Additional workstations could be provided. For example, a workstation with its own client PC, display, keyboard, mouse and barcode scanner could be provided at work surface 103 of modules 29-31. Such a workstation could simply provide extra working space for a pharmacist, pharmacy technician or other authorized user, or there could be ranked storage locations positioned with respect to the additional workstation. Storage devices other than modules 23-35 may be utilized. For example, rotatable carousels could be used in place of base-type enclosures 80 with pull-out drawers (e.g., drawers 93-101). Shelving units 89 could by utilized to provide fixed-position storage locations for system 11. By way of further example, refrigerated storage devices can be provided for perishable pharmaceutical products, and locked, controlled-access storage devices can be provided for controlled substances such as narcotics.

Pharmaceutical Product Container Adaptive Storage

Management of an inventory of pharmaceutical product containers (e.g., containers 13, 15, 17, 18, 19) by system 11 may be based on one or more of several operational modes. The exemplary modes are referred to herein as a Continually Optimized Location (COL) mode, Periodic Optimized Location (POL) mode, a Seasonally Optimized Location (SOL) mode, an Alphabetically Organized Location (AOL) mode, a User Organized Location (UOL) mode, and a Special Rules (SR) mode. One mode of operation may be used for management of containers (e.g., containers 13-19) for certain pharmaceutical products while a different mode of operation may be used for management of containers (e.g., containers 13-19) for other pharmaceutical products.

The COL, POL and SOL modes are based on, and adapt to, actual and/or anticipated frequency of use of the pharmaceutical products by the pharmacy. The AOL and UOL modes permit pharmacy user determination of storage locations (e.g., locations 37-59). The SR mode provides an additional level of user control for special cases. Each mode enables system 11 to accurately track the quantity, type, lot number and expiration date of each pharmaceutical product in inventory. The COL, POL and SOL modes direct storage and track movement of the pharmaceutical product containers (e.g., containers 13-19) among the storage locations (e.g., locations 37-59) from induction into system 11 until the container (e.g., containers 13-19) is removed from system 11. The objective of these modes is to direct placement of each pharmaceutical product container (e.g., containers 13-19) to a storage location having an ease-of-accessibility ranking commensurate with the usage frequency ranking of the pharmaceutical product, making those containers for the pharmaceutical products used most frequently most easily accessible to workstation 21.

In the COL mode, the storage location (e.g., locations 37-59) of a pharmaceutical product container (e.g. containers 13-19) within system 11 is determined by frequency of use. If containers and storage locations are grouped into subsets according to type, the usage frequency determination is based on rankings within each subset. The storage location of each pharmaceutical product container may change after each prescription fulfillment transaction involving the selected container (e.g., container 13-19).

In the POL mode, system 11 operates as in the COL mode but the rate of change of storage locations is slowed down as determined by the user. The purpose of the POL mode is to retain products in locations familiar to the user while at the same time adapting to changes in usage frequency subject to a user-determined time constraint described below.

In the SOL mode, the storage location of a pharmaceutical product container (e.g. containers 13-19) within system 11 is determined by frequency of use and anticipated seasonal variation of demand. The SOL and POL modes are the same except that usage frequencies are determined dependent on whether a product is identified by pharmacy as being in or out of season.

The AOL and UOL modes permit the pharmacy to determine the storage location of each pharmaceutical product. If desired, these modes may be used in combination with the COL, POL and SOL modes for certain of the pharmaceutical products stored at the pharmacy.

In the AOL mode, the storage location of a pharmaceutical product container (e.g. containers 13-19) within system 11 is determined by pharmaceutical product name. This mode of operation permits pharmacy to locate certain products alphabetically for convenience.

In the UOL mode, the storage location of a pharmaceutical product container (e.g. containers 13-19) within system 11 is determined by pharmacy preferences. The UOL mode of operation lets the pharmacy select the storage location for specific pharmaceutical products without constraint. In the UOL mode, system 11 creates a record of the storage location (e.g., locations 37-59) at which each pharmaceutical product container (e.g. container 13-19) is stored, and system 11 is configurable so that the pharmacy may assign each pharmaceutical product container to a specific storage location.

In the Special Rules (SR) mode, the user determines any special rules that may apply to storage of certain pharmaceutical product containers. The SR mode may be used in combination with other modes. For example, the SR mode permits particular pharmaceutical products to be designated for use only by certain patients. A particular product could be designated as accessible only for patients participating in a government-sponsored health-care program. The location of the product could change based on usage frequency but the product itself may only be accessible to a limited group of patients.

A method of adaptive management of pharmaceutical products by a pharmacy will now be described with respect to the flow diagrams of FIGS. 9A-9D. The method includes placement of pharmaceutical product containers (e.g. containers 13-19) into storage locations (e.g., locations 37-59) of system 11 and further includes picking of containers and fulfillment of prescription orders. The method which will be described is representative of the adaptive behavior of the COL mode. Variations of the COL mode provided by the POL and SOL modes are also described as are the AOL, UOL and SR modes.

Figure 9A:
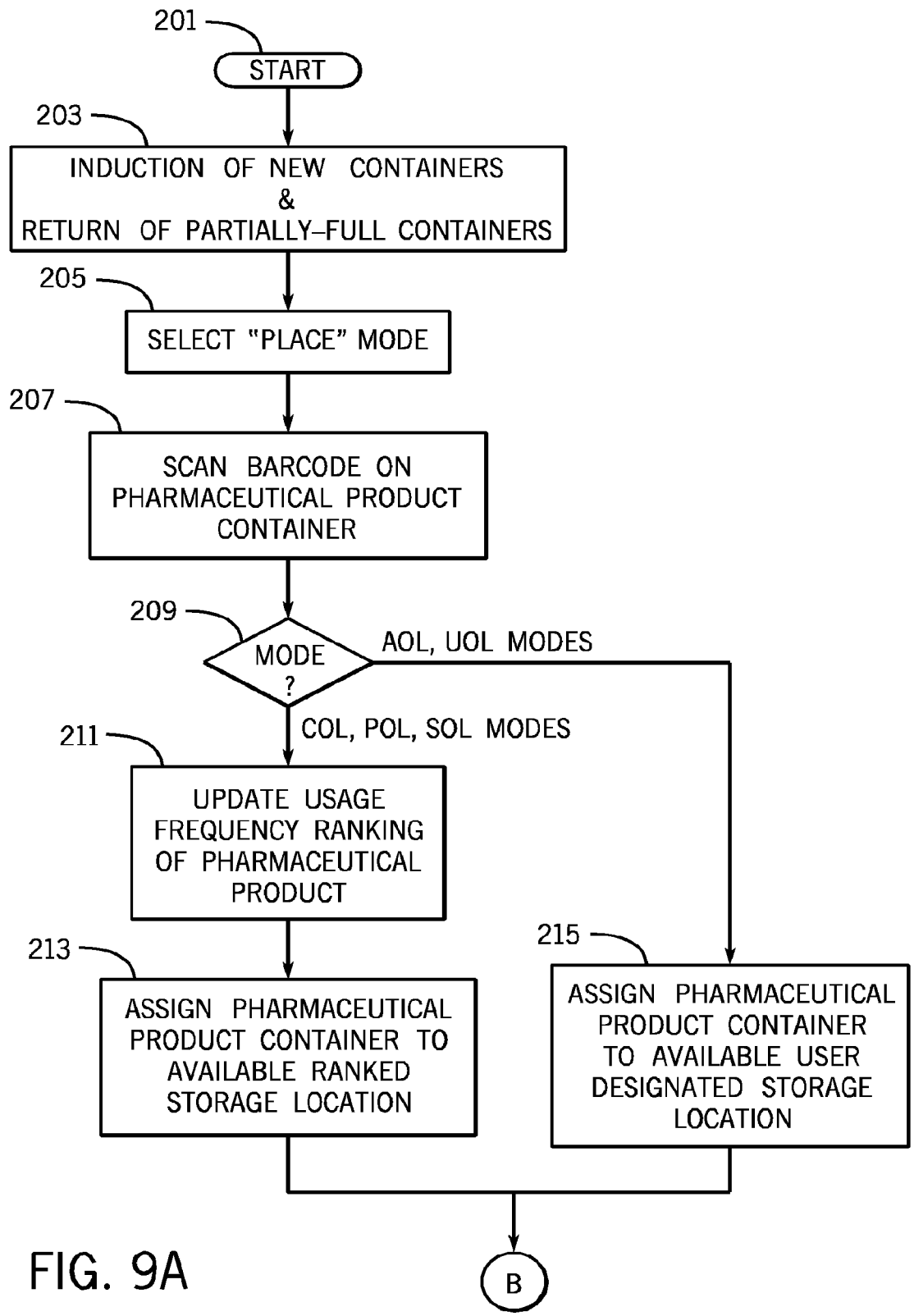
FIGS. 9A, 9B, 9C and 9D are flow diagrams showing an exemplary method of adaptive pharmaceutical product storage management.
Figure 9B:
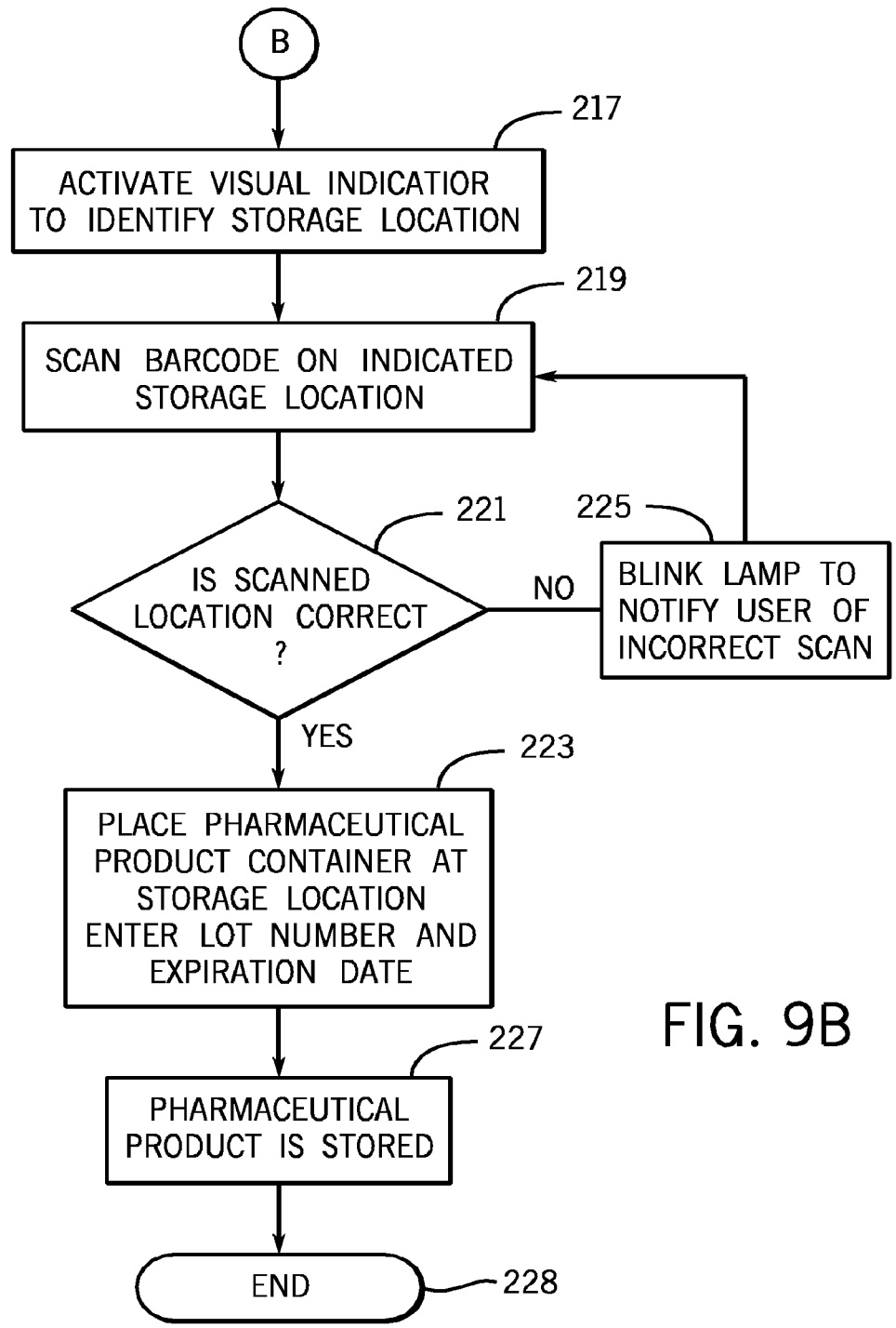

FIGS. 9A and 9B, illustrate a process implemented by system 11 for placement of pharmaceutical product containers (e.g., containers 13-19) into the storage locations (e.g., locations 37-59) of system 11. The process illustrated in FIGS. 9A and 9B may be used for the initial placement of each pharmaceutical product container (e.g., containers 13-19) into a storage location (e.g., locations 37-59) when system 11 is first placed into operation. If COL, POL, SOL or SR modes are implemented for the initial placement of pharmaceutical product containers into storage when system 11 is first placed into operation, then historical usage frequency data from prescriptions filled by the pharmacy would be used for the ranking of each pharmaceutical product. The ranking is used so that pharmaceutical product containers (e.g., containers 13-19) for the pharmaceutical products are assigned to ranked storage locations having an ease-of-accessibility ranking commensurate with the usage frequency ranking of the pharmaceutical product as described in blocks 211 and 213. If UOL, AOL (or SR) modes are implemented for the initial placement of pharmaceutical product containers into storage when system 11 is first placed into operation, then the initial storage locations are determined by the pharmacy based on pharmacy preference or alphabetical organization as described in connection with block 215.

While not preferred, it is also possible that the pharmacy could place the pharmaceutical product containers (e.g., containers 13-19) randomly into storage locations (e.g, locations 37-59) when system 11 is first placed into operation because the process implemented by system 11 will cause the inventory of pharmaceutical product containers (e.g., containers 13-19) to adapt over time so that the storage location ease-of-accessibility ranking for each pharmaceutical product container will be commensurate with the usage frequency ranking of the pharmaceutical product stored therein.

A database record of the storage location of each pharmaceutical product container is made in database 73 every time a container is stored by system, including at the point when system 11 is first placed into operation, as described in block 223. Based on the database record in database 73, the storage location (e.g., locations 37-59) of every pharmaceutical product container (e.g., containers 13-19) is identified by system 11 from the point at which system 11 is first placed into operation and forward.

The process illustrated in FIGS. 9A and 9B continues to be used as new, unopened pharmaceutical product containers (e.g., containers 13-19) are inducted into the inventory of pharmaceutical product containers stored by means of system 11 and as partially-full pharmaceutical product containers are returned to storage after use for fulfillment of prescriptions by the pharmacy.

Referring then to FIG. 9A, the process performed by system 11 for placement of pharmaceutical product containers into storage locations is entered at Start 201. At block 203, the user has one or more pharmaceutical product containers (e.g., container 13-19) to place into system 11. The user may be, for example, a restocking clerk whose responsibilities include placing new containers and partially-full containers into the pharmacy inventory. New, unopened pharmaceutical product containers (e.g., containers 13-19) may, for instance, be unpacked by a user from a manufacturer's shipping container, while partially-full pharmaceutical product containers (e.g., containers 13-19) may be from a restocking bin 167 in which the partially-full container was placed after use for prescription fulfillment by another user such as a pharmacist or pharmacy technician. Use of a restocking bin 167 to collect plural partially-full containers (e.g., containers 13-19) is a matter of convenience and efficiency only; partially-full containers may also be returned to storage on an individual basis without use of a restocking bin 167.

At block 205, the user at workstation 21 sets system 11 to a "place" mode by inputting the appropriate command to controller 63 by means of an input device such as touchscreen display 65, keyboard 67 or mouse 69. At block 207, the user scans barcode 157 on a pharmaceutical product container (e.g., containers 13-19) with barcode scanner 71. The data string from barcode scanner 71 is output to controller 63. Controller 63 database 73 may use a relational database to match the data string to the exact manufacturer, pharmaceutical product type, package type and pharmaceutical product quantity, thereby accurately identifying the pharmaceutical product container (e.g., container 13-19) and creating a record in database 73. If required, the human-readable 159 NDC embedded in bar code 157 could be manually entered into database 73 by a user to identify the container (e.g., container 13-19) to database 73.

At decision point 209, system 11 determines the user-selected mode designated for the pharmaceutical product in the pharmaceutical product container (e.g., container 13-19). Database 73 is used to determine that a pharmaceutical product has been designated by the pharmacy as being in one of the six modes (COL, POL, SOL, AOL, UOL, SR). If the mode is determined to be either the COL, POL or SOL, the process proceeds to block 211. If the mode is determined to be either the AOL or UOL mode, the process proceeds to block 215. SR mode can apply to the process at blocks 211-213 or block 215. The mode determination for each pharmaceutical product is made as each pharmaceutical product is first inducted into system 11 but may be modified at any point thereafter.

Referring next to blocks 211 and 213, before each new container (e.g. containers 13-19) or partially-full pharmaceutical product container (e.g. containers 13-19) is placed into storage, a storage location is determined for the container by system 11 based on the pharmacy's usage frequency of the pharmaceutical product in the container. The storage location is an initial storage location at the time when system 11 is first placed into operation or when a new pharmaceutical product is first introduced into inventory and is an updated storage location for induction of a new container of a pharmaceutical product already in inventory or for a partially-full container being returned to inventory after prescription fulfillment in block 251.

The storage location is assigned with the objective of aligning the pharmaceutical product's usage frequency ranking with the storage location's ease of accessibility ranking so that the most frequently used pharmaceutical products are assigned to the storage locations most easily accessible to workstation 21. For a new product not previously in inventory, an estimate of anticipated usage frequency would be performed to accomplish this assignment. A further objective of system 11 is to provide an updated storage location with a ranking which is: (1) more easily accessible than previously-ranked storage locations for the same pharmaceutical product if the product's usage frequency ranking is increasing, (2) about as easily accessible as previously-ranked storage locations for the same pharmaceutical product if the product's usage frequency ranking is relatively constant, or (3) less easily accessible than previously-ranked storage locations for the same pharmaceutical product if the product's usage frequency ranking is decreasing.

The first step of this process occurs at block 211. At block 211, the usage frequency ranking of the pharmaceutical product being placed is updated (or determined for new products) in the COL, POL and SOL modes according to the rules for each mode. The SR mode may also apply. In the COL mode, usage frequency ranking is determined by rank-ordering each pharmaceutical product in the COL category (within subsets if subsets are being used), from highest to lowest usage frequency, based on the frequency of usage within a moving time window. The frequency of usage determination is based on prescription fulfillment transactions rather than total tablets used (i.e., the number of prescriptions for each pharmaceutical product). Preferably, the moving time window is a period of one year. So, for example, the usage frequency for the pharmaceutical product is determined, and the ranking based on usage frequency is then determined within the rank ordering which applies to the set or subset. Usage data of each pharmaceutical product is determined from the database 73 of all pharmacy transactions within the moving-window time period. A record of each pharmaceutical product usage is automatically created at block 251 each time the pharmaceutical product is used to fulfill a patient prescription. Historical usage information from the pharmacy can be used during the first year of system 11 operation if a one year moving time window period is utilized. Estimated usage frequency could be determined for new products not previously in inventory.

System 11 maintains a rank-ordering of usage frequencies and determines the usage frequency ranking within this rank-ordering each time a pharmaceutical product is placed into inventory. Therefore, a pharmaceutical product which has been used to fill 1,000 prescriptions during the moving-window time period has a usage frequency ranking higher in the rank-ordering than all of the pharmaceutical products having a usage less than 1,000 times within the time period of the last assessment of usage frequency. In other words, a pharmaceutical product with a ranking of 1 is used more frequently by a pharmacy than a pharmaceutical product with a ranking of 10.

For the POL mode, the determination of the usage-frequency ranking of the pharmaceutical product designated as POL only occurs if the time since the last change of storage location exceeds a user-determined time period, also referred to herein as a time constraint. Usage data continues to be collected, as in the COL mode. However, if this user-determined time period has not elapsed, the container is simply assigned back to the storage location from which it was picked in block 215. The result is to slow movement of the POL-designated pharmaceutical products in inventory. POL mode may be useful for users who prefer to become familiar with the location of certain pharmaceutical products.

For the SOL mode, additional information is taken into account at block 211 to determine the usage frequency ranking of the seasonally-designated pharmaceutical product. Initially, a determination has been made that the pharmaceutical product is a seasonal product and the product has been so identified in database 73. If a pharmaceutical product is seasonal, its usage-frequency ranking is annualized for the designated season so that the ranking of the seasonal pharmaceutical product is adjusted commensurate with its historical seasonal usage. After the season, the ranking of the seasonal pharmaceutical product is adjusted commensurate with its historical off-season usage. Like the POL mode, the usage-frequency ranking of a seasonal product is determined at a user-determined time which is typically the beginning of the season and end of the season. The user-determined time is a time constraint based on seasonal usage. The usage-frequency ranking is preferably subject to the time constraint and is not modified further during the season and off season.

As an example of the SOL mode of operation, an antihistamine could be categorized as seasonal for the spring and summer seasons. The antihistamine could have a very low usage frequency ranking in the fall and winter seasons but a high usage frequency ranking in the spring and summer seasons. Average usage frequency of the antihistamine over a one-year moving-window period would result in a ranking lower than that reflective of the seasonal usage and a ranking greater than the off season usage. By annualizing the in-season and off-season data, system 11 immediately anticipates the appropriate changes in the usage frequency ranking of the seasonal product so that the product can receive the appropriate seasonal usage-frequency ranking in block 211. This seasonal usage-frequency adjustment results in storage of the seasonal pharmaceutical product at the storage location (e.g., locations 37-59) commensurate with the seasonal usage-frequency ranking as described in connection with block 213.

The second step of the process occurs at block 213. At block 213, controller 63 next assigns an available storage location (e.g., location 37-59) to the usage-frequency-ranked pharmaceutical product (based on prescription transactions, not total tablets used). The goal of this assignment is to place each pharmaceutical product container (e.g., container 13-19) at a storage location which is ranked with respect to ease-of-accessibility to workstation 21 at approximately the same ease-of-accessibility ranking as its ranking with respect to usage frequency.

Each storage location within system 11 is assigned an ease-of-accessibility ranking at the time of system setup as previously described. These rankings result in a rank-ordering of all storage locations (e.g., location 37-59) within a set, or subset if plural sizes or other types of locations are provided. Therefore, a storage location that is more easily accessible has a ranking higher in the rank-ordering of ease-of-accessibility than all of the storage locations which are judged to be less-easily accessible. By way of example and as previously described, storage locations in a drawer 97 at a convenient height in module 25 at workstation 21 could have a higher (i.e., more favorable) ranking than storage locations in a drawer 115 in module 35 spaced from workstation 21.

The initial or updated storage location for the pharmaceutical product container is determined as follows in block 213. Assume that the usage frequency for the pharmaceutical product has a ranking of R within a total rank-ordering range of from 1 to P, where P is the total number of pharmaceutical products in the set or subset and 1 is the most favorable ranking. The pharmaceutical product which has a usage frequency ranking of R+1 is stored at a location having an ease-of-accessibility ranking of E, and the pharmaceutical product which has a usage frequency ranking of R−1 is stored at a location having an ease-of-accessibility ranking of E-$\Delta$. E and E-$\Delta$, are in the rank-ordering range of from 1 to L, where L is the total number of storage locations in the set or subset and 1 is the most favorable ranking. The symbol $\Delta$ represents the difference in numerical rank of the storage locations. Storage locations (e.g., locations 37-59) which are more easily accessible to workstation 21 have a better ranking. In other words, a storage location with a ranking of 1 is deemed more easily accessible than a storage location with a ranking of 10. Therefore, the storage location ranking represented by E-$\Delta$, is more favorable than the storage location represented by E.

As previously described, L is always greater than P, and L-P is the excess number of storage locations. The excess of storage locations represents a cache of available storage locations within a set or subset. L-P should be large enough to provide an adequate number of available storage locations to permit the adaptive behavior of the COL mode to function. As an example only, L-P may represent approximately 4% to approximately 10% of the total storage locations L.

At block 213, system 11 attempts to identify an available storage location with an ease-of-accessibility ranking between E and E-$\Delta$ under the constraint that there be at least X available storage locations within the group of Y storage locations in which the available storage location falls. For example, for Y=100 and X=4, groups of 100 are defined by storage location ease-of-accessibility rankings of from 1-100, 101-200, 201-300, etc. The 4% minimum of available storage locations of each group would form the cache or buffer which allows the adaptive behavior of the placement system to function. If an available storage location satisfies the constraint, the pharmaceutical product container will be placed randomly in one of the available storage locations within the range of E and E-$\Delta$. This designated storage location is the initial or updated storage location for the pharmaceutical product container.

If there are no available storage locations which satisfy the constraints, then an available storage location is sought between the storage locations having an ease-of-accessibility ranking of between, for example, E-$\Delta$ and E-$\Delta$-Z, where Z is a number of storage locations with more favorable rankings above ranking E-$\Delta$. For example, Z=100 means the one hundred storage locations having an ease-of-accessibility ranking more favorable than E-$\Delta$. If no available storage locations are within this category, then an available storage location is sought between the storage locations having an ease-of-accessibility ranking between E+1 and E+Z. This process is repeated, looking in alternating fashion above and below in the rankings, until an available storage location is identified.

The choice for first looking outside the initial range (i.e., the initial range is between E and E-$\Delta$) for an available storage location with an ease-of-accessibility ranking more favorable in the range is called the "more-favorable-first strategy." In order to more evenly distribute available storage locations throughout the range of storage locations in a set or subset, system 11 may include the use of both the "more-favorable-first strategy" and a "less-favorably-first strategy." The less-favorable-first strategy is the inverse of that which was described for the more-favorable-first strategy. System 11 may be user-configured to alternate between the more-favorable and less-favorable-first strategies, for example, based on even and odd days of the calendar or some other means of determining alternation. So for example, the more-favorable-first strategy is implemented on an even calendar day, and the less-favorable-first strategy is implemented on an odd calendar day. The storage location assigned to the pharmaceutical product container resulting from application of either the more-favorable- or less-favorable-first strategies would represent the initial or updated storage location.

It is possible that two different pharmaceutical products can have the same usage-frequency ranking resulting in a type of ranking "tie." An illustrative example can be used to illustrate the method performed by system 11 in the event of a tied pharmaceutical product ranking Assume that a hypothetical pharmaceutical product "A" and a hypothetical pharmaceutical product "B" each have been used 500 times in a given moving-window usage-frequency determination in block 211. In this illustrative example, both hypothetical pharmaceutical products might have a usage frequency ranking of "10." If there were other ties, the next pharmaceutical product having a more-favorable ranking than 10 could be ranked "4," and the next pharmaceutical product having a less favorable ranking than 10 could be ranked "12." Since there would be no ranked pharmaceutical product equivalent to either rankings R+1 and R−1 in this example, system 11 defaults to the next more favorable ranked pharmaceutical product and the next less favorable ranked pharmaceutical product and proceeds to perform the storage location determination as described above based on the storage locations of the next more-favorable and next less-favorable ranked pharmaceutical products.

This same storage location placement methodology is used within each subset of storage location and pharmaceutical product subsets. So, the subset of refrigerated storage location types is stocked with perishable pharmaceutical products as just described, and so on, for each pharmaceutical product size or type and storage location type.

Referring further to block 213, controller database 73 includes a record of the unique barcode 141 along the bottom wall 135 of the assigned fixed-position storage location (e.g., location 37-59). The unique barcode 141 is used in a subsequent step 219 to confirm that the pharmaceutical product container (e.g., container 13-19) has been correctly placed in the assigned initial or updated storage location (e.g., locations 37-59).

The lower portion of FIG. 8 illustrates a highly simplified example of storage location assignment based on changes in pharmaceutical product usage frequency. Twelve storage locations are represented from modules 25, 31 and 35. Each location is ranked from 1 to 12 based on ease of access to workstation 21 as indicated in each storage location. As the usage-frequency ranking of the pharmaceutical product in container 13 increases or decreases relative to usage frequency rankings of other pharmaceutical products in the inventory set or subset, the ease-of-accessibility ranking of the updated storage location of container 13 is changed. In this highly simplified example, if usage frequency increases sufficiently, container 13 could move from the 8th-ranked storage location to the 3rd-ranked storage location. If usage frequency decreases sufficiently, container 13 could move from the 5th-ranked location to the 9th-ranked location and so on.

In this way, system 11 assigns updated storage locations representing adaptation to changes in usage of pharmaceutical products by the pharmacy resulting in convenient and efficient storage distribution of the pharmaceutical product containers relative to the workstation 21. New and partially-full containers with a pharmaceutical product being used more frequently (on a rank-order basis) migrate to storage locations more easily accessible (on a rank-order basis) to the workstation 21 while those pharmaceutical products which are experiencing decreased usage frequency migrate to storage locations less easily accessible to workstation 21.

Referring now to block 215 of FIG. 9A, block 215 is entered if the pharmaceutical product in the pharmaceutical product container (e.g., containers 13-19) is to be placed into inventory using either of the AOL, UOL or SR modes. The AOL and UOL modes do not require any determination of the priority of the pharmaceutical product (block 211) because the user has already designated the storage locations to which the container should be placed either based on alphabetical sorting using each pharmaceutical product's name (AOL mode) or based on other user-designated storage location determinations (UOL mode). The user-designated storage locations for each pharmaceutical product container are maintained in database 73.

As in block 213, the assigned storage location (e.g., location 37-59) represents the initial or updated storage location. Controller database 73 includes a record of the unique barcode 141 associated with the initial or updated storage location used in the confirmation step in block 219 below.

At block 217, for each of the COL, POL, SOL, AOL, UOL and SR modes, the assigned storage location is indicated to the user by means of OPS system 75 and activation of the appropriate visual indicator 79. Controller 63 outputs a signal to visual indicator controller 77 which activates the visual indicator 79 at the assigned storage location. Lamp 145 is energized to indicate the drawer into which the pharmaceutical product container (e.g., containers 13-19) should be placed. Visual indicator controller 77 also activates displays 147, 149 to indicate respectively, the row and column of the storage location (e.g., locations 37-59) into which the pharmaceutical product container is to be placed.

Use of multi-color-emitting LED lamps 145 as illustrated in FIGS. 7A, 7B and 7C and as previously described in connection with OPS 75, would enable multiple users to simultaneously place pharmaceutical product containers into inventory and to pick pharmaceutical product containers to fulfill patient prescription orders.

At block 219, the user accesses the indicated assigned storage location and scans barcode 141 along the bottom wall 135 of the assigned storage location with barcode scanner 71. The barcode 141 data string is output from barcode scanner 71 to controller 63.

At decision point 221, controller 63 determines whether the scanned storage location is correct for the storage location. The storage location is correct if the scanned barcode data string from scanning of the storage location barcode 141 at block 219 matches the expected barcode data string for the assigned storage location from block 213 (for COL, POL and SOL modes) or block 215 (For AOL and UOL modes). If there is a match, the process proceeds to block 223.

If there is no match, then at block 225 controllers 63, 77 send a signal to visual indicator 79 of OPS system 75 causing lamp 145 to blink. The blinking lamp 145 is indicative that the user selected the wrong storage location. The blinking lamp 145 prompts the user to return back to block 217 and to scan the barcode 141 of the correct storage location. If the repeat of blocks 217 and 219 results in further blinking of lamp 145 at block 225, then the user must stop the process and determine the source of the error.

At block 223, the user places the pharmaceutical product container into the indicated storage location. The user may manually enter the lot number 163 and expiration date 165 of the container into controller 63 by means of touch-screen display 65, keyboard 67 or mouse 69 so that the lot number 163 and expiration date 165 are associated with the record for the container in database 73. A record of the date and time of placement of the pharmaceutical product container into the storage location based on the match at point 221 is created in database 73. Database 73 now includes a complete record of the pharmaceutical product stored at the indicated storage location including the pharmaceutical product type and quantity, the container size, and the lot number and expiration date of the pharmaceutical product. Database 73 is also updated so that the total quantity of the pharmaceutical product type in inventory, including the quantity of pharmaceutical product just added to inventory, is known.

At block 227, the pharmaceutical product container is deemed stored in system 11 at its initial or updated storage location and the process ends at 228.

Pharmaceutical Product Container Selection and Prescription Fulfillment

Figure 9C:
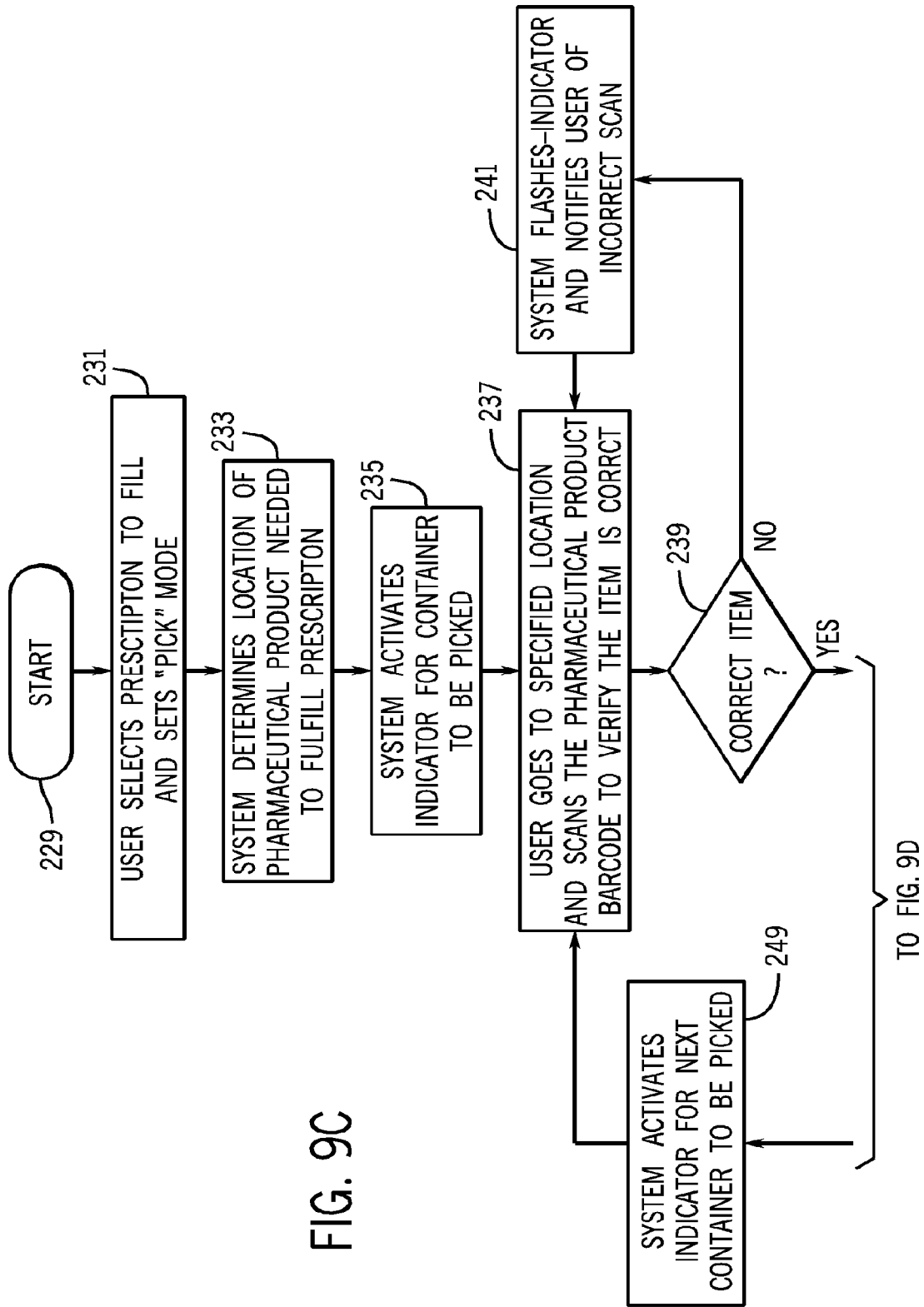
Figure 9D:
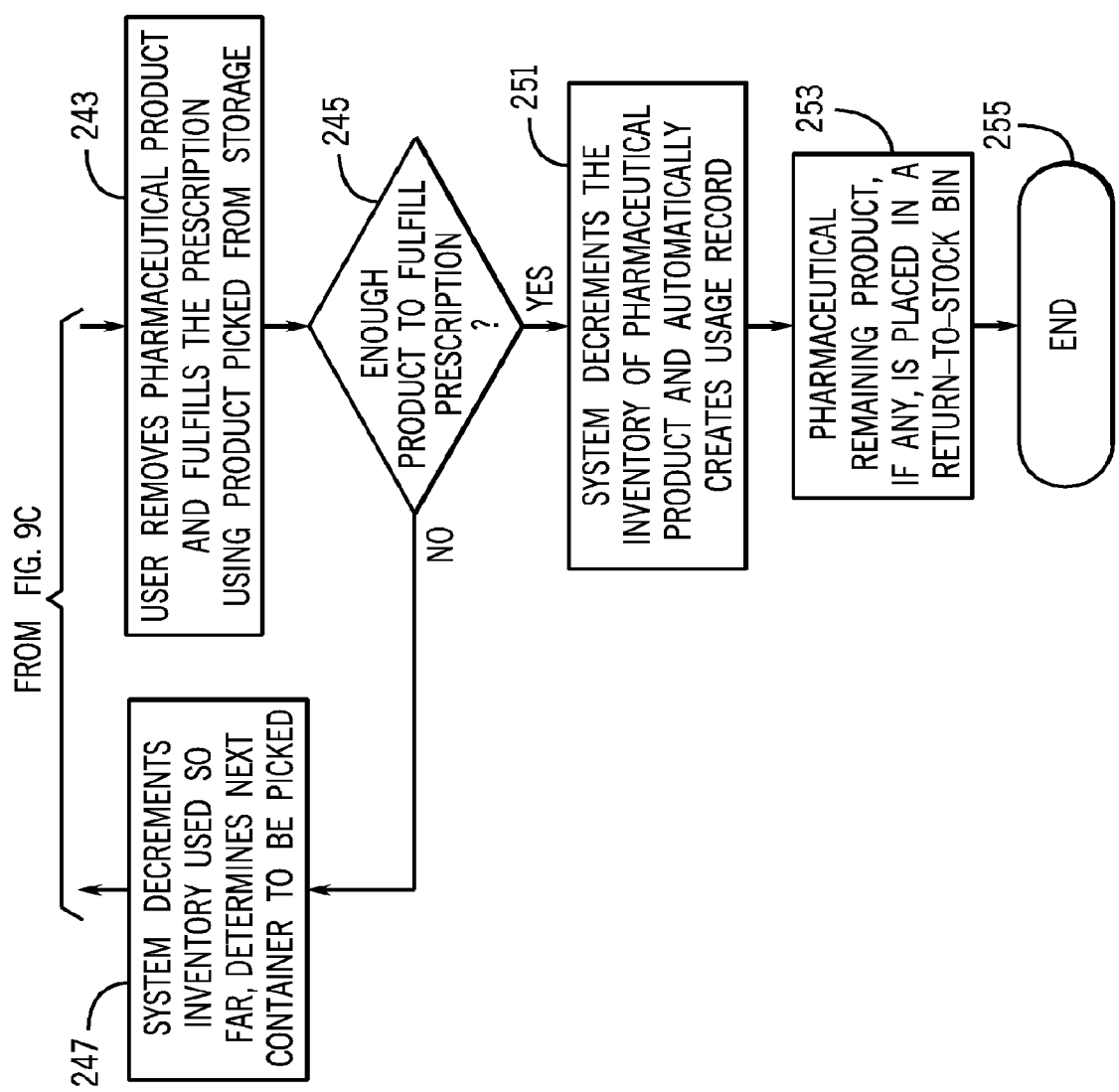

Referring now to FIGS. 9C and 9D, a process for prescription fulfillment and selection of the pharmaceutical product container containing the required pharmaceutical product is described. The process is entered at start 229. At block 231, a user at workstation 21 sets system in a "pick" mode in the same manner as selection of the "place" mode in block 205. Also in block 231, the user selects a patient prescription for fulfillment. Selection of a prescription for fulfillment may be accomplished in any suitable manner such as by scanning a barcode on prescription paperwork generated by the pharmacy (not shown) with barcode scanner 71 or selecting a prescription displayed on display 65 with mouse 69. The selection is output to controller 63 which accesses a record in database 73 for the prescription which includes the pharmaceutical product type, strength, and quantity required to fulfill the patient prescription.

At block 233, controller 63 determines the storage location (e.g., locations 37-59) at which a pharmaceutical product container (e.g., containers 13-19) containing the required product is located. Because the full and partially-full pharmaceutical product containers (e.g., containers 13-19) were preferably put away based on actual usage frequency, and/or anticipated usage frequency based on seasonal usage, the containers most likely to be needed to fulfill the prescription will be most easily and efficiently accessible to the user at workstation 21. If the AOL or UOL modes were used, the pharmaceutical product container is at a user-designated storage location.

Determination of the storage location can include consideration of expiration date or the date a drug was entered into inventory for cases in which there are plural containers of the same pharmaceutical product in inventory. As previously described, lot number 163 and expiration date 165 can be entered into database 73 at block 223 so as to enable FEFO-based (first-expiration, first-out) inventory management. System 11 can determine the storage location of the container for the pharmaceutical product closest to expiration so that such container and product is used first to fulfill the patient prescription. A FIFO-based rule (first-in, first-out) can be applied in the same way using the date that the pharmaceutical product was first placed into inventory.

SR mode designation for a pharmaceutical product may result in identification of a pharmaceutical product container according to special user-determined rules. One special rule example is limiting access to a particular pharmaceutical container to a select group of pharmacy patients, such as persons who are participants in a particular health-care program.

At block 235, the determined storage location is indicated to the user by activation of the appropriate visual indicator 79. Controller 63 outputs a signal to visual indicator controller 77 which activates the OPS system 75 visual indicator 79 at the determined storage location. Lamp 145 is energized to indicate the drawer from which the pharmaceutical product container (e.g., containers 13-19) should be picked. Visual indicator controller 77 also activates displays 147, 149 to indicate respectively, the row and column of the storage location (e.g., locations 37-59) from which the pharmaceutical product container is to be picked (e.g., FIG. 7A or 7B or 7C).

At block 237, the user goes to the indicated storage location (e.g., locations 37-59), picks the pharmaceutical product container (e.g., container 13-19) from the location and scans the container barcode 157 with barcode scanner 71. The barcode 157 data string is output from barcode scanner 71 to controller 63.

At decision point 239, controller 63 determines whether the scanned barcode data string from block 237 matches the expected barcode for the pharmaceutical product associated with the patient prescription residing in the record for the prescription in database 73. If there is a match, the process proceeds to block 243.

If there is no match, then at block 241 controller 63 sends a signal to visual indicator 79 causing lamp 145 to blink. The blinking lamp 145 is indicative that the user selected the wrong pharmaceutical product container (e.g., container 13-19). The blinking lamp 145 prompts the user to return back to block 237 and to rescan the barcode 157 of the pharmaceutical product container. If the repeat of blocks 237 and 239 results in further blinking of lamp 145 at block 241, then the user must stop the process and determine the source of the error.

At block 243, the user removes the pharmaceutical product container (e.g., 13-19) and initiates fulfillment of the patient prescription at workstation 21 with the selected pharmaceutical product container.

A result of blocks 237, 239 and 243 is that controller 63 database 73 is updated to indicate that the pharmaceutical product container (e.g., container 13-19) has been removed from the indicated storage location. The now-unoccupied storage location is available to store a pharmaceutical product container and is added to the cache of available storage locations. Database 73 is updated to reflect that the now-available storage location is part of the cache.

At decision point 245, a determination is made regarding whether there is sufficient pharmaceutical product in the selected pharmaceutical product container (e.g., container 13-19) with which to fulfill the patient prescription. This could be a particular issue when a partially-full container has been designated to be picked from storage by controller 63. If there is sufficient pharmaceutical product, then the process proceeds to block 251.

Block 247 is entered if there is insufficient pharmaceutical product in the selected pharmaceutical product container. The user enters the quantity of pharmaceutical product available in the selected container into controller 63 by means of touch-screen display 65, or keyboard 67, or mouse 69. At block 247, controller 63 decrements the quantity of pharmaceutical product used thus far from the total count of the pharmaceutical product in inventory. The now-empty pharmaceutical product container can be discarded.

Continuing with block 247, controller 63 determines the storage location (e.g., locations 37-59) at which another pharmaceutical product container (e.g., containers 13-19) containing the required product is located. Preferably this further pharmaceutical product container was also put away based on implementation of the COL, POL and/or SOL modes so as to be easily and efficiently accessible to the user at workstation 21 based on frequency of use of the pharmaceutical product.

At block 249, the determined storage location is indicated to the user by activation of the appropriate visual indicator 79 of OPS system 75 as previously described for block 235.

Blocks 237, 241, 243 and point 239 are repeated as previously described until the result of decision point 245 is yes indicative that sufficient pharmaceutical product has been obtained to fulfill the prescription. Thereafter, block 251 is entered.

At block 251, controller 63 decrements the total count of the pharmaceutical product from inventory and automatically records the prescription fulfillment transaction in database 73 including the date, time, medication type and quantity provided in fulfillment of the prescription. This record of medication and quantity usage is used in subsequent usage-frequency rankings at step 211 as previously described in order to provide an updated storage location to the next full or partially-full container being placed into storage.

At block 253, if any pharmaceutical product remains in the pharmaceutical product container (e.g., container 13-19) after counting out the quantity required to fulfill the patient prescription, then the closure 153 or 155 is placed back on the container, and the container is placed into a restock bin 167 to await return to inventory. Alternatively, the user could immediately return the partially-full container to inventory by following the process previously described with respect to steps 201-227. If all of the pharmaceutical product has been removed from the container then the container can be discarded.

The process ends at 255. A further prescription can now be selected for fulfilment and the process of blocks/decision points 229-255 is repeated until all prescriptions in a prescription order are fulfilled.

Another aspect of the system 11 and methods performed by system 11 is lot number and expiration date tracking. As previously described, the lot number 163 and expiration date 165 of each pharmaceutical product container can be entered into database 73 of controller 63 at block 223. Database 73 continuously associates the lot number 163 and expiration date 165 with the pharmaceutical product container from the point of induction of the into system 11 (block 227) until the container is removed from inventory or discarded (block 253). As previously described, controller 63 can designate that pharmaceutical product be selected from inventory on a FEFO basis so as to maintain active pharmaceutical product in the pharmacy inventory and to ensure that patients are provided with the highest-quality pharmaceutical product.

In addition to providing FEFO-type inventory management, controller 63 can alert the user in advance of the expiration date 165 by, for example, displaying a message on display 65, so that the container (e.g., container 13-15) can be removed from inventory by the user and returned for refund to the manufacturer. This is particularly useful for pharmaceutical products which are used infrequently and which may exist in partially-full containers in inventory. The alerts can be provided at any user-configurable time increment or increments in advance of the expiration date 165.

The monetary refund paid by the manufacturer to the pharmacy for returned pharmaceutical product can be greater if relatively more time exists before the expiration date. By providing an alert or alerts about the expiration date, the pharmacy is able to timely determine whether pharmaceutical product containers (e.g., containers 13-19) should be removed from inventory and returned to the manufacturer for refund. Pharmaceutical product refunds can represent a significant source of income to the pharmacy, particularly when the alternative is to simply discard unused expired pharmaceutical products.

Tracking of lot number 163 provides the user with a further degree of control over the pharmaceutical products in inventory that would not be available if the lot number 163 of each pharmaceutical product in inventory was not known. For example, if a batch of a pharmaceutical product is recalled by the manufacturer, the user can enter the lot number 163 into controller 63 and database 73 will identify the storage location (e.g., locations 37-59) of each pharmaceutical product container (e.g., containers 13-19) with that lot number. Visual indicator controller 77 can activate the relevant visual indicator 79 or indicators 79 to indicate the storage location (e.g., containers 13-19) to a user. The identified pharmaceutical product containers could then be easily removed from storage and returned to the manufacturer.

Lot number tracking also permits the pharmacy to identify any patient who has been provided with pharmaceutical product from the relevant lot because the lot number 163 from the container (e.g., containers 13-19) used to fulfill the prescription is associated with each fulfilled prescription in database 73. In the event of a recall, the pharmacy can contact each patient and advise the patient to return any unused pharmaceutical product.

Another aspect of system 11 and the methods performed by system 11 is management of the inventory of pharmaceutical product containers (e.g., containers 13-19) in a way which provides improved security and theft-deterrence. Although very much the exception, there have been instances of theft of pharmaceutical products stored in the inventory of pharmaceutical product containers (e.g., containers 13-19). Entire containers (e.g., containers 13-19) can be taken or separate tablets can be taken from a container.

As previously noted, a benefit of the dense storage provided by system 11 is that pharmaceutical product containers (e.g., containers 13-19) are not required to be grouped together by pharmaceutical product type and can be distributed among any of the storage locations (e.g., locations 37-59) which can accommodate the container size and pharmaceutical product type.

This distribution is a theft deterrent for several reasons. One reason is that particular pharmaceutical product containers (e.g., containers 13-19) can be difficult to locate. Pharmaceutical product containers tend to be look-alike monochromatic plastic bottles as illustrated in FIGS. 2A and 2B. And, the storage locations (e.g, locations 37-59) of system 11 can look alike. Consequently, containers for more theft-prone pharmaceutical products are difficult to readily distinguish from any other container. Since the pharmaceutical product containers (e.g., containers 13-19) are not required to be stored at a specific shelf location and since the containers tend to look alike, the more theft-prone pharmaceutical products can, in effect, be concealed among the containers forming the inventory of pharmaceutical product containers. And, system 11 can be configured to require movement of high-value containers (e.g., narcotics, viagra, etc.) to a new storage location (e.g., locations 37-59) each time the container is touched. Thus, system 11 provides a deterrent against theft by "hiding" or "camouflaging" more theft-prone containers among the entirety of all other containers stored by system 11.

While the principles of this invention have been described in connection with specific embodiments, it should be understood clearly that these descriptions are made only by way of example and are not intended to limit the scope of the invention.

What is claimed is:

1. An adaptive pharmaceutical product storage system for storage of pharmaceutical product containers within a pharmacy, the system comprising:

a pharmacy workstation at which a human pharmacy user performs manual tasks associated with fulfillment of prescription orders by the pharmacy;

at least one pharmaceutical product storage device positioned with respect to the workstation;

a plurality of pharmaceutical product storage locations associated with the at least one storage device, each storage location defining a space for storing a pharmaceutical product container and having a unique address, each storage location further having a ranking based on relative ease-of-accessibility to the workstation;

a visible indicator proximate each of the storage locations which guides the user to an indicated storage location for placing and picking a container at the indicated storage location;

a processor to control each of the indicators and having a database including the unique address and ease-of-accessibility ranking of each storage location, the storage location of each container and a usage frequency ranking of each pharmaceutical product, the processor configured to:

control the visible indicator of the storage location for the pharmaceutical product required for prescription fulfillment to guide movement of the user to the indicated storage location for picking of the container;

update the database to indicate use of the pharmaceutical product;

determine a usage frequency ranking of the pharmaceutical product;

determine an updated storage location for the container if pharmaceutical product remains in the container or for a further container of the pharmaceutical product based on the updated usage frequency ranking such that the updated storage location has an ease-of-accessibility ranking commensurate with the updated usage frequency ranking; and operate the visible indicator of the updated storage location to guide movement of the user to the indicated updated storage location for placing the container at the indicated updated storage location, whereby the containers are stored at storage locations having an ease-of-accessibility ranking commensurate with the usage frequency ranking of the pharmaceutical product and more frequently used pharmaceutical products are more easily accessible to the user working from the workstation.

2. The system of claim 1 wherein the at least one storage device is selected from the group consisting of a storage module, a shelving unit, a cabinet and combinations thereof.

3. The system of claim 1 wherein the visible indicator is associated with the storage device such that the visible indicator is visible to the user together with the storage device.

4. The system of claim 3 wherein the visible indicator includes at least one lamp.

5. The system of claim 4 wherein the at least one lamp is operable to output a color of a plurality of colors, the output color being associated with one user to direct such one user, and not other users, to the storage location.

6. The system of claim 3 wherein the visible indicator further includes at least one numeric display which indicates the storage location to the user.

7. The system of claim 1 wherein the ease-of-accessibility rankings are based on time required for the user to access the storage locations from the workstation.

8. The system of claim 1 wherein the ease-of-accessibility rankings are based on relative distance of the storage locations from the workstation.

9. The system of claim 1 wherein the ease-of-accessibility rankings are based on human factors required to access the storage locations.

10. The system of claim 1 wherein the storage locations are grouped into subsets and the ease-of-accessibility rankings are determined within each subset.

11. The system of claim 1 wherein the processor is further configured to determine the usage frequency ranking of the pharmaceutical product during a moving window time period.

12. The system of claim 11 wherein the moving window time period is one calendar year.

13. The system of claim 12 wherein the processor is further configured to determine the usage frequency ranking of the pharmaceutical product based on prescription fulfillment transactions of the pharmaceutical product during the moving window time period.

14. The system of claim 1 wherein the processor is further configured to associate an expiration date with the pharmaceutical products in the containers.

15. The system of claim 14 wherein the processor is further configured to indicate the storage location of the container having an earlier expiration date before the storage location of a container of the same pharmaceutical product having a later expiration date.

16. The system of claim 1 wherein the processor is further configured to associate a lot identifier with the pharmaceutical product in the containers and to indicate the storage location of the containers by the lot identifier.

17. The system of claim 1 wherein the processor is further configured to include user-selectable modes selected from the group consisting of (1) a mode in which the rate of change of storage location is slowed and (2) a further mode in which the storage location is determined based on anticipated seasonal demand of the pharmaceutical product.

18. The system of claim 1 wherein the processor is further configured to maintain a plurality of empty storage locations to facilitate movement of the containers.

19. An adaptive pharmaceutical product storage system for storage of pharmaceutical product containers within a pharmacy, the pharmaceutical product storage system comprising:

a pharmacy workstation including a work surface at which a human pharmacy user performs manual tasks associated with fulfillment of prescription orders by the pharmacy;

at least one pharmaceutical product storage device arranged with respect to the workstation;

a plurality of pharmaceutical product storage locations associated with the at least one storage device, each storage location defining a space for storing a pharmaceutical product container and having a unique address, each storage location further having a ranking based on relative ease-of-accessibility to the workstation;

a visible indicator proximate each of the storage locations which guides the user to an indicated storage location for placing and picking a container at the indicated storage location;

a processor to control each of the indicators and having a database including the unique address and ease-of-accessibility ranking of each storage location, the storage location of each container and a usage frequency ranking of each pharmaceutical product, the processor configured to:

determine a usage frequency ranking of the pharmaceutical products based on relative use of the pharmaceutical products by the pharmacy to fulfill prescriptions within a moving window time period;

assign a storage location when a partially-full container is returned to storage and when a full container is placed into storage based on the usage frequency ranking such that the assigned storage location has an ease-of-accessibility ranking commensurate with the determined usage frequency ranking and more frequently used pharmaceutical products are more easily accessible to the user working from the workstation;

operate the visible indicator of the storage location to guide movement of the user thereto for placing the container at the indicated storage location; and operate the visible indicator of the storage location to guide movement of the user thereto for picking the container at the indicated storage location.

20. The system of claim 19 wherein the assigned storage location has a greater ease-of-accessibility ranking if the pharmaceutical product is determined to have a greater usage frequency.

21. The system of claim 19 wherein the assigned storage location has a lesser ease-of-accessibility ranking if the pharmaceutical product is determined to have a lesser usage frequency.

22. The system of claim 19 wherein the usage frequency ranking determination is based on prescription fulfillment transactions using the pharmaceutical product.

23. The system of claim 19 wherein the at least one storage device is selected from the group consisting of a storage module, a shelving unit, a cabinet and combinations thereof and the visible indicator is associated with the at least one storage device such that the visible indicator and at least one storage device are simultaneously visible to the user.

24. The system of claim 19 wherein the processor is further configured to update the database by associating a code of the indicated storage location with a code of the container placed at the indicated storage location.

25. The system of claim 24 wherein the codes are barcodes, the system further includes a barcode reader and the processor is further configured to update the database by associating the barcode of the indicated storage location with the barcode of the container placed at the indicated storage location.

26. The system of claim 19 wherein the processor is further configured to maintain a plurality of empty storage locations to facilitate movement of the containers.

\* \* \* \* \*